(12) United States Patent
Hammock et al.

(10) Patent No.: US 7,176,280 B2
(45) Date of Patent: Feb. 13, 2007

(54) **ISOLATED POLYPEPTIDES AND COMPOSITIONS FROM THE VENOM OF *P. TRANSVAALICUS* AND METHODS OF USE**

(75) Inventors: Bruce D. Hammock, Davis, CA (US); Bora Inceoglu, Ankara (TR)

(73) Assignee: The Regents of the University of California, Oakland, CA (US)

( * ) Notice: Subject to any disclaimer, the term of this patent is extended or adjusted under 35 U.S.C. 154(b) by 467 days.

(21) Appl. No.: 10/264,480

(22) Filed: Oct. 4, 2002

(65) Prior Publication Data
US 2003/0113892 A1 Jun. 19, 2003

Related U.S. Application Data

(60) Provisional application No. 60/327,602, filed on Oct. 4, 2001, provisional application No. 60/393,070, filed on Jun. 28, 2002.

(51) Int. Cl.
C07K 7/06 (2006.01)
C07K 11/00 (2006.01)
C07K 14/00 (2006.01)
C07K 1/14 (2006.01)
C12N 15/62 (2006.01)

(52) U.S. Cl. ............... 530/324; 530/328; 530/412; 435/69.7; 435/252.3; 435/320.1

(58) Field of Classification Search ........... 530/300, 530/324–329, 314, 350; 514/2, 12, 13, 14, 514/15, 16, 17
See application file for complete search history.

(56) References Cited

U.S. PATENT DOCUMENTS

2004/0031072 A1* 2/2004 La Rosa et al. ............ 800/278

FOREIGN PATENT DOCUMENTS

| WO | WO 00/24772 A3 | 5/2000 |
| WO | WO 00/32777 A3 | 6/2000 |
| WO | WO 00/78957 A3 | 12/2000 |
| WO | WO 00/78958 A3 | 12/2000 |

OTHER PUBLICATIONS

Swerts et al. Development and optimization of a purification strategy go the venom of the scorpion *Parabuthus transvaalicus*. 1997. Journal de pharmacie de Belgique 52 (5): 194-195.*
Debont et al. Comparison and characterization of the venoms of three *Parabuthus* scorpion species occuring in Southern Africa. Feb. 1998. Toxicon 36 (2):341-352.*

(Continued)

*Primary Examiner*—Kathleen Kerr
*Assistant Examiner*—William W. Moore
(74) *Attorney, Agent, or Firm*—James S. Keddie; Bozicevic, Field & Francis

(57) ABSTRACT

The invention provides isolated polypeptides from the venom of the scorpion *P. transvaalicus*. The invention also provides novel scorpion antivenom compositions derived from such polypeptides, as well as methods for isolating the polypeptides and preparing scorpion antivenom compositions. The isolated polypeptides can be used to produce pharmaceutical compositions useful for treating diseases and conditions associated with ion channel function or kinin activity.

13 Claims, 12 Drawing Sheets

Figure 4A:
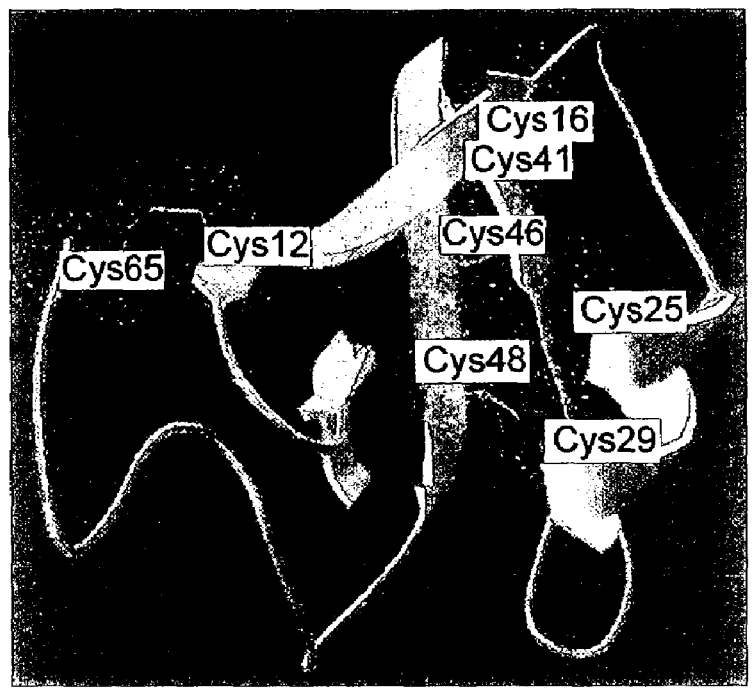

```
Lysyl-bradykinin-like      KRPPGWSPLR  (SEQ ID NO: 31)
Bradykinin-like            M.KRSRGPSPRR (SEQ ID NO: 32)
Waspkinin                  QZKRPPGFSPFRK (SEQ ID NO: 33)
Megascoliakinin             RPPGFTPFRKA (SEQ ID NO: 34)
_Thr6_bradykinin            RPPGFTPFR  (SEQ ID NO: 35)
Vespulakinin           TATTRRRG.RPPGFSPFR (SEQ ID NO: 36)
Maximakinin         DLPKINRKGPRPPGFSPFR (SEQ ID NO: 37)
Bradykinin                  RPPGFSPFR  (SEQ ID NO: 38)
Parakinin1                    PFIVPPFR  (SEQ ID NO: 27)
Parakinin2                    PFVVPPFR  (SEQ ID NO: 29)

Consensus 1                rppgXXPfR
Consensus 2                $^{m}X_1X_2X_3X_4X_5PX_6R$
Consensus 3              $X_1(X_2)_nX_3X_4X_5X_6PX_7R$
```

OTHER PUBLICATIONS

Inceoglu et al. "A single charged surface residue modifies the activity of ikitoxin, a beta-type Na+ channel toxin from *Parabuthus transvaalicus*," *Eur. J. Biochem.*, 2002, vol. 269, No. 2, pp. 5369-5376.
Inceoglu et al. "Isolation and characterization of a novel type of neurotoxic peptide from venom of the South African scorpion *Parabuthus transvaalicus* (Buthidae)," *Eur. J. Biochem.*, 2001, vol. 268, No. 20, pp. 5407-5413.
Chuang et al. "Inhibition of T-type voltage-gated calcium channels by a new scorpion toxin," *Nature Neuroscience*, 1998, vol. 1, No. 8, pp. 668-674.
Campbell et al., Clin. Exp. Pharm. Phys., 2001, (28): 1060-1065.
Couture et al, European J. Pharmacology, 2001, (429):161-176.
Fatani et al.. Toxicon. 1998. (3):523-36.
Ferreira et al., Toxicon, 1998, (36):31-39.
GenBank Accession Nos. P42717 Bethesda : National Library of Medicine 1995.
GenBank Accession Nos. 1601326C Bethesda : National Library of Medicine 1988.
GenBank Accession Nos. S39030 Bethesda : National Library of Medicine 1993.
GenBank Accession Nos. P12797 Bethesda : National Library of Medicine 1989.
GenBank Accession Nos. 0504194A Bethesda : National Library of Medicine 1979.
GenBank Accession Nos. A61339 Bethesda : National Library of Medicine 1976.
GenBank Accession Nos. CAD29346 Bethesda : National Library of Medicine 2005.
GenBank Accession Nos. CAC48026 Bethesda : National Library of Medicine 2001.
Ismail et al., Toxicon, 1992, (10):1257-79.
Kotovych et al Biochem, Cell Bio., 1998, (76): 257-266.
Meki et al., Peptides, 1995, 16(8):1359-65.

* cited by examiner

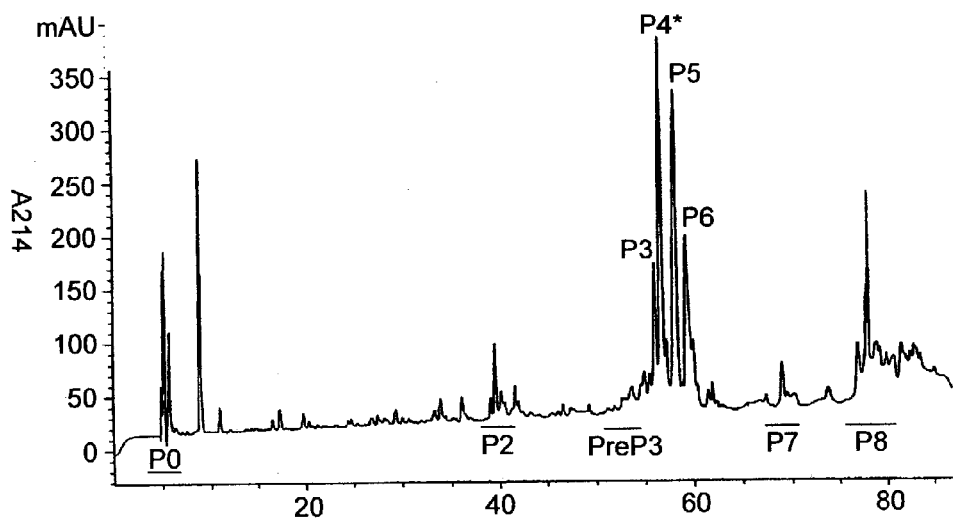
FIG. 1
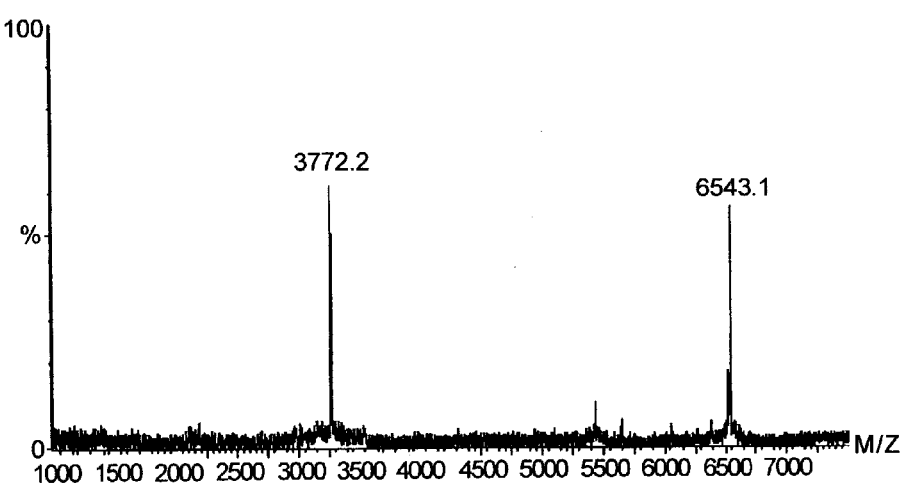
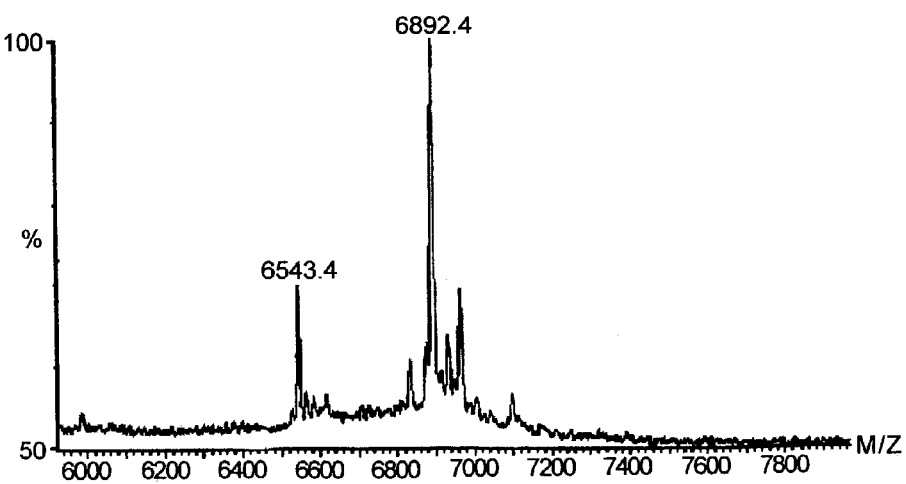

FIG. 3

GLY23

GLU23

FIG. 11

Enhancement of [³H] BTX binding to rat brain synaptosomes by birtoxin of *Parabuthus transvaalicus*

Birtoxin: ADVPGNYPLDKDGNTYKCFLLGGNEECLNVCKLHGVQYGYCYASKCWCEYLEDDKDSV
[SEQ ID NO: 1]

FIG. 12

Enhancement of [$^3$H] BTX binding to rat brain synaptosomes by uctoxin of *Parabuthus transvaalicus*

Uctoxin: KKDGYPVDHANCKYECWYNNVYCNDLCKKLKANHGYCYGYNLA [SEQ ID NO: 5]

| | |
|---|---|
| Lysyl-bradykinin-like | KRPPGWSPLR (SEQ ID NO: 31) |
| Bradykinin-like | M.KRSRGPSPRR (SEQ ID NO: 32) |
| Waspkinin | QZKRPPGFSPFRK (SEQ ID NO: 33) |
| Megascoliakinin | RPPGFTPFRKA (SEQ ID NO: 34) |
| _Thr6_bradykinin | RPPGFTPFR (SEQ ID NO: 35) |
| Vespulakinin | TATTRRRG.RPPGFSPFR (SEQ ID NO: 36) |
| Maximakinin | DLPKINRKGPRPPGFSPFR (SEQ ID NO: 37) |
| Bradykinin | RPPGFSPFR (SEQ ID NO: 38) |
| Parakinin1 | PFIVPPFR (SEQ ID NO: 27) |
| Parakinin2 | PFVVPPFR (SEQ ID NO: 29) |
| | |
| Consensus 1 | rppgXXPfR |
| Consensus 2 | $^{m}X_1X_2X_3X_4X_5PX_6R$ |
| Consensus 3 | $X_1(X_2)_nX_3X_4X_5X_6PX_7R$ |

FIG. 13

ISOLATED POLYPEPTIDES AND COMPOSITIONS FROM THE VENOM OF *P. TRANSVAALICUS* AND METHODS OF USE

CROSS-REFERENCE

This application claims the benefit of U.S. Provisional Patent Application No. 60/327,602, filed Oct. 4, 2001, and U.S. Provisional Patent Application No. 60/393,070, filed Jun. 28, 2002, which applications are incorporated herein by reference in their entirety.

GOVERNMENT RIGHTS

This invention was made with Government support under Grant Nos. 2001-35302-09919 and 97-35302-4406 awarded by the USDA, Grant No. R37ES02710 awarded by the NIEHS and Grant No. P42ES04699 awarded by the NIEHS Superfund Basic Research Program. The Government has certain rights in this invention.

FIELD OF THE INVENTION

The present invention relates generally to scorpion venom compositions and methods of preparing and using the compositions.

BACKGROUND OF THE INVENTION

Scorpions are distributed throughout the tropical and subtropical belts of the world in habitats ranging from dry deserts to the mountains. Only a fraction of the existing species have venom potent enough to endanger humans and almost all of these are found in the family Buthidae. Those considered most dangerous are found in the Middle East, Asia, South America, and Africa. *Parabuthus transvaalicus* is a large (up to 150 mm) South African scorpion species from the family Buthidae and considered to be medically important (Bergman (1997) *Toxicon* 35:759–771). The victims of a sting by *P. transvaalicus* can suffer from neurotoxic effects, prolonged pain, which lasts from one day in minor cases and up to a week in severe cases, and even death. Symptoms include abnormal reflexes, bladder symptoms, dysphagia, sweating and hypersalivation (Bergman, N. J. (1997), supra).

Venom of *P. transvaalicus* is a 'simple' venom compared to other scorpion venoms because it contains less than 100 major peptides. The venom may be characterized by defining the individual components of the system (identification of peptide toxins), analysis of the structure of the components (primary, secondary and tertiary structure determination), analysis of the function of each component (determination of the mode of action), analysis of the relationships between these components (synergism) and the target sites or the environment (binding sites and kinetics).

Although poisonous scorpions are sprinkled across several genera taxonomically, the action of the venom is similar. Scorpion venoms are a rich source of neurotoxic peptides with diverse modes of action. Within the complex mixture of venoms, peptides have been found to possess the majority of the biological effect towards the sting victims; however, these peptides are usually low in abundance (Nakagawa (1997) *Eur. J. Biochem.* 246:496–501). Stings manifest themselves mostly in the peripheral nervous system, resulting in symptoms such as intense pain at the sting site, altered heart activity, and parasthesia. Stings to children, the elderly, and unhealthy individuals are much more dangerous and more often lethal. Where antivenom is available, it is very effective in counteracting the effects of the sting, and when administered, victims are typically asymptomatic within 90 minutes.

Current methods for antivenom production involve the direct injection into horses of crude venom or antibodies produced from a mixture of a number of species' venom. However, there are risks associated with the injection of antibodies from another animal, or passive immunization. The recipient can mount a strong immunologic response to the isotypic determinants of the foreign antibody. This anti-isotype response can have serious complications because some recipients will produce IgE antibody specific for the injected passive antibody. Immune complexes of IgE bound to the antibody can mediate systemic mast cell degranulation, leading to systemic anaphylaxis. Another possibility is that the recipient will produce IgG or IgM antibodies specific for the foreign antibody, which will form complement-activating immune complexes. The deposition of these complexes in the tissues can lead to type III hypersensitive reactions.

In addition, the small polypeptides in the venom are frequently not able to elicit a strong immunogenic reaction from the host. Potent neurotoxins, which often are relatively small and low abundance molecules, may not always induce the production of sufficient quality and quantity of antibody molecules. Therefore, a balance between the injected dose, the toxicity towards the subject animal and high quality antibody production has to be obtained, often empirically, every time a new batch of antivenom is produced. Identification of less abundant, but highly potent components in a purified venom mixture has advantages, compared to using the crude venom as antigen to raise antibodies for therapeutic purposes.

Scorpion venoms contain many small protein neurotoxins that act selectively on various types of voltage-gated ion channels. These neurotoxins affect the victim by interfering with neuronal ionic balance and channel activity. Ion channels are multi-subunit, membrane bound proteins critical for maintenance of cellular homeostasis in nearly all cell types. Channels are involved in a myriad of processes including modulation of action potentials, regulation of cardiac myocyte excitability, heart rate, vascular tone, neuronal signaling, activation and proliferation of T-cells, and insulin secretion from pancreatic islet cells. In humans, ion channels comprise extended gene families with hundreds, or perhaps thousands, of both closely related and highly divergent family members. The majority of known channels regulate the passage of sodium ($Na^+$), chloride ($Cl^-$), calcium ($Ca^{++}$) and potassium ($K^+$) ions across the cellular membrane.

Binding of scorpion toxins to target ion channels is known to occur through multiple interactions (Rogers et al. (1996) *J. Biol. Chem.* 271:15950–15962) Numerous amino acid residues have been determined to have effect on binding (Possani et al. (1999) *Eur. J. Biochem.* 264:287–300). In addition, alpha scorpion toxins are known to slow or inhibit sodium channel inactivation. Recently their mechanism of action at the molecular level on sodium channels became more apparent. These site 3 binding toxins bind to the extracellular S3-S4 loop of the domain IV, a major part of the voltage sensor, on the sodium channel and alter the transmembrane movement of this region which is required in the gating process (Cestele and Catterall (2000) *Biochimie* (Paris) 82:883–892.).

Given their importance in maintaining normal cellular physiology, it is not surprising that ion channels have been shown to play a role in heritable human disease. Indeed, ion channel defects are involved in predisposition to epilepsy, cardiac arrhythmia (long QT syndrome), hypertension (Bartter's syndrome), cystic fibrosis, (defects in the CFTR chloride channel), several skeletal muscle disorders (hyperkalemic periodic paralysis, paramyotonia congenita, episodic ataxia) and congenital neural deafness (Jervell-Lange-Nielson syndrome), among others.

Recently, a toxin called margatoxin was isolated from the venom of Centruroides margaritatus. Margatoxin is very potent and selectively binds to one subtype of potassium channel produced by human T-lymphocytes (Lin et al. (1993) J. Exp. Med. 177:637–645). Margatoxin may be useful in treating autoimmune diseases or in preventing the rejection of organ transplants (WO 95/03065). Another neurotoxin known in the art is Botox®, or botulinum toxin type A, which is a muscle-relaxing agent that works at the motor nerve endings. Botox® is used in treating neuromuscular problems, cervical dystonia, strabismus and blepharospasm. Botox® is also used in the cosmetic dermatology industry to prevent wrinkle formation (see U.S. Pat. No. 5,721,215). Although these toxins and many others have been useful as experimental tools, they are not particularly selective in their actions on different tissues and they affect a variety of subtypes of ion channels.

In addition to their effects on ion channels, scorpion venoms are also known to modulate the kinin pathway in animals. Kinins are nonapeptides generated as a result of the activity of killikreins, a group of proteolytic enzymes present in most tissues and body fluids, on kinonogens. Once released, kinins such as bradykinin and related peptides kallikin (Lys-bradykinin) and Met-Lys-bradykinin produce many physiological responses, including pain and hyperanalgesia, in addition to contributing to the inflammatory response (reviewed in Couture et al Eur. J. Pharm. 429: 161–176 2001 and Campbell et al Clin. Exp. Pharm. Phys. 28: 1060–1065 2001). In addition, bradykinin is overproduced in a very wide range of pathological conditions, and is thought to be a contributing factor in septic shock, asthma, and can also increase the permeability of the blood-brain barrier and thereby promote the passage of anti-infectious or antitumoral drugs. How scorpions modulate the kinin pathway in animals is, as yet, unknown.

Accordingly, there is a need to characterize the compositions of scorpion toxins not only in order to develop more effective antivenoms, but also to understand human and animal physiological responses to the venoms. The characterization of particular toxins that are involved in ion channel regulation or kinin responses are of particular interest as ion channels and kinins are involved in many other conditions and diseases. The present invention addresses these needs and many others.

Also of interest are the following publications: WO 00/78958, EP 1185654, WO 00/78957, EP 1185653, WO 00/32777, WO 00/24772, EP1124954, Couture et al, European J. Pharmacology 429 161–176, 2001; Kotovych et al Biochem. Cell Bio. 76:257–266, 1998; Campbell, Clinical and Experimental Pharmacology and Physiology 28:1060–1065, 2001; and Ferreira et al., Toxicon 36:31–39, 1998.

SUMMARY OF THE INVENTION

The invention provides isolated polypeptides from the venom of the scorpion P. transvaalicus. The invention also provides novel scorpion antivenom compositions derived from such polypeptides, as well as methods for isolating the polypeptides and preparing scorpion antivenom compositions. The isolated polypeptides can be used to produce pharmaceutical compositions useful for treating diseases and conditions associated with ion channel function or kinin activity.

The method of the invention generally involves characterizing the venom of various scorpion species and isolating the polypeptides of interest from the various fractions. The identification, isolation and characterization of novel birtoxin and parakinin families of toxins is described.

One embodiment of the invention is novel families of isolated and characterized scorpion venom toxins. These scorpion toxins are separated from their natural milieu and used in methods of the invention to identify compounds that modulate birtoxin family polypeptide-ion channel binding or kinin activities. Compositions comprising a pharmaceutically acceptable carrier and an isolated scorpion venom toxin are further provided.

A further aspect of the invention is isolated scorpion venom toxin-encoding polynucleotides. Scorpion venom toxin-encoding polynucleotide sequences can be operatively inserted into cells and used to produce scorpion toxin family polypeptides, and are further useful in detecting hybridizing polynucleotides, and can therefore be used to detect the presence of and/or measure a level of scorpion toxin-encoding mRNA in a biological sample, as well as to detect related polynucleotides. Recombinant vectors and host cells comprising the isolated polynucleotides are further provided.

Another aspect of the invention are antibodies which specifically bind a scorpion venom toxin. Such antibodies are useful in assays to detect the presence of a scorpion venom toxin, and are further useful in altering birtoxin family polypeptide-ion channel binding or kinin activity.

A further aspect of the invention are modulators of birtoxin family polypeptide-ion channel or kinin-kinin receptor interactions. Such modulators are useful identifying agents with potential pharmaceutical uses.

Yet another aspect of the invention are assays which detect the presence and/or level of scorpion toxin-encoding mRNA, in a biological sample. In another aspect, the invention provides assays for detecting the presence and/or level of a scorpion toxin in a biological sample.

The invention further provides a variety of methods for detecting agents which modulate birtoxin family polypeptide levels or birtoxin family polypeptide-ion channel interactions. Thus, the invention provides assays for determining compounds which modulate birtoxin family polypeptide-ion channel interactions, including compounds which inhibit and compounds which enhance birtoxin family polypeptide-ion channel interactions. The present invention also provides methods for modulating a level of birtoxin family polypeptide and/or birtoxin family mRNA in a cell. Methods for detecting agents which modulate kinin levels and/or kinin/kinin-receptor interactions. Thus, the invention provides assays for determining compounds which modulate kinin/kinin-receptor interactions, including compounds which inhibit and compounds which enhance kinin/kinin-receptor interactions. The present invention further provides methods for modulating a level of parakinin family mRNA or polypeptide in a cell.

An advantage of the invention is that compounds found to modulate birtoxin family polypeptide-ion channel interactions are candidates for the treatment of diseases or disorders associated with ion channel function. Accordingly, in one aspect, the invention provides methods of treating various forms of diseases and disorders associated with ion channel function.

A further advantage of the invention is that compounds found to modulate kinin/kinin-receptor interactions are candidates for the treatment of diseases or disorders associated with kinin activity. Accordingly, in one aspect, the invention provides methods of treating various forms of diseases and disorders associated with kinin activity.

Another aspect of the invention is contacting an insect or pest with a composition comprising a scorpion venom toxin to kill or alter the behavior of the insect or pest. Accordingly, scorpion venom toxins can be used for insecticide or pesticide activities.

Another aspect of the invention is contacting cells with a birtoxin family polypeptide in order to effect cellular ion channel function to obtain a desired change in function and/or the study channel function before and after the birtoxin is administered.

Another aspect of the invention is antivenom composition for treating scorpion envenomation. An advantage of the antivenom composition of the invention is that the antivenom may be produced at a consistent level of toxicity, such that a standardized dose may be given without extensively testing each antivenom batch prepared.

Another advantage of the composition of the invention is that antivenom of sufficient effectiveness may be prepared from antibodies to a relatively small polypeptide, preferably a scorpion venom toxin. Still another advantage of the composition of the invention is that the scorpion venom toxin will not cause anaphylactic shock in a subject.

Another aspect of the invention is that the isolated scorpion toxin may be administered to the victim of a scorpion sting to provide a prophylactic effect.

These and other objects, advantages, aspects, and features of the invention will become apparent to those persons skilled in the art upon reading the details of the invention as more fully described below.

BRIEF DESCRIPTIONS OF THE DRAWINGS

FIG. 1. Chromatograph of the separation of crude venom by RP-HPLC using a C4 column. Individual peaks are collected, dried and used for mass determination and bioassays. In the case of P3, P4, P5 and P6 the apparent peaks were collected separately. In other fractions, bars show the region of the chromatogram that were combined for subsequent assay. Birtoxin was predominantly in fraction P4.

FIG. 2A and FIG. 2B. Mass spectra of native and reduced and carboxymethylated birtoxin. Molecular masses were determined by MALDI-TOF. Native birtoxin (FIG. 2A) and modified birtoxin (FIG. 2B) were both purified using a C18 column on the Microbore HPLC. After reduction and carboxymethylation, modified birtoxin was re-purified using the same column. Native birtoxin was used as an internal standard for the mass determination of the modified birtoxin. The observed mass (6892.4) for the modified birtoxin was in agreement with the expected mass of six cysteine residues being carboxymethylated.

Figure 3:
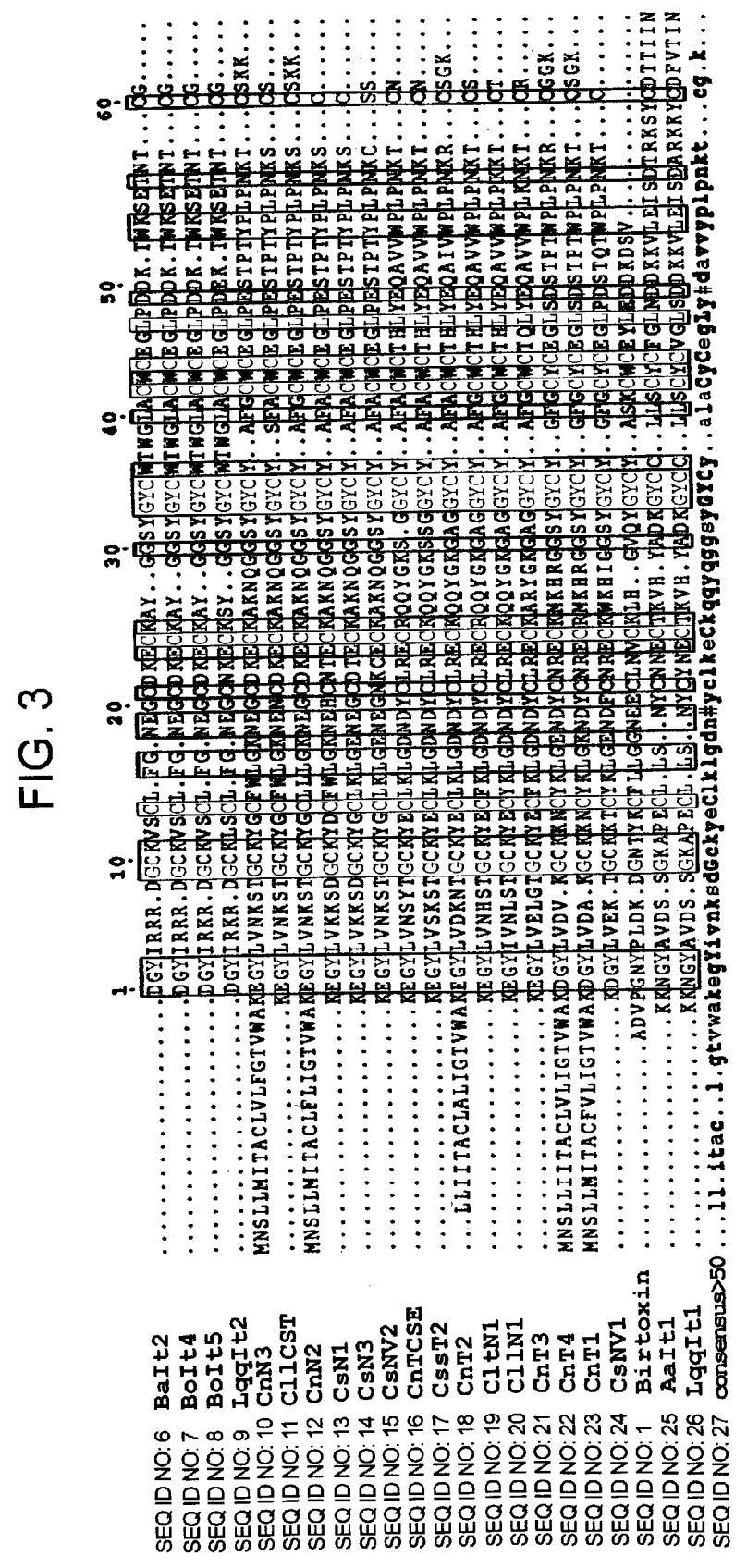

FIG. 3. Amino acid sequence alignment comparison of known polypeptides with birtoxin. Primary sequence of birtoxin was aligned with known polypeptides using ClustalW program and visualized using the EsPriPt tool (SEQ ID NOS:6–27). Known scorpion toxins used in the comparison and percent identities with birtoxin were as follows: BaIt2 (Buthus arenicola Depresant insect toxin 2) 48% identity, BoIt4 (Buthus occitanus insect toxin 4) 48% identity, BoIt5 (Buthus occitanus insect toxin 5) 47% identity, LqqIt2 (Leiurus quinquestriatus quinquestriatus Insect Toxin 2) 45% identity, CnN3 (Centruroides noxius CNGTIII Precursor) 53% identity, ClICST (Centruroides limpidus limpidus crustacean specific toxin) 51% identity, CnN2 (Centruroides noxius CNGTII Precursor) 52% identity, CsN1 (Centruroides sculpturatus Neurotoxin 1) 42% identity, CsN3 (Centruroides sculpturatus Neurotoxin 3) 52% identity, CsNV2 (Centruroides sculpturatus Neurotoxin 2) 48% identity, CnTCSE (Centruroides noxius Toxin CSE M1) 47% identity, CssT2 (Centruroides suffusus suffusus Toxin 2) 47% identity, CnT2 (Centruroides noxius Toxin 2 precursor) 47% identity, CltN1 (Centruroides limpidus tecomanus Neurotoxin 0.1) 47% identity, ClIN1 (Centruroides limpidus limpidus Neurotoxin 1) 47% identity, CnT3 (Centruroides noxius Toxin 3) 48% identity, CnT4 (Centruroides noxius CNGTIV precursor) 42% identity, CnT1 (Centruroides noxius Toxin 1 precursor) 40% identity, CsNV1 (Centruroides sculpturatus Neurotoxin 1) 54% identity, AaIt1 (Androctonus australis Insect toxin 1) 38% identity, and LqqIt1 (Leiurus quinquestriatus quinquestriatus Insect Toxin 1) 38% identity.

Figure 4B:
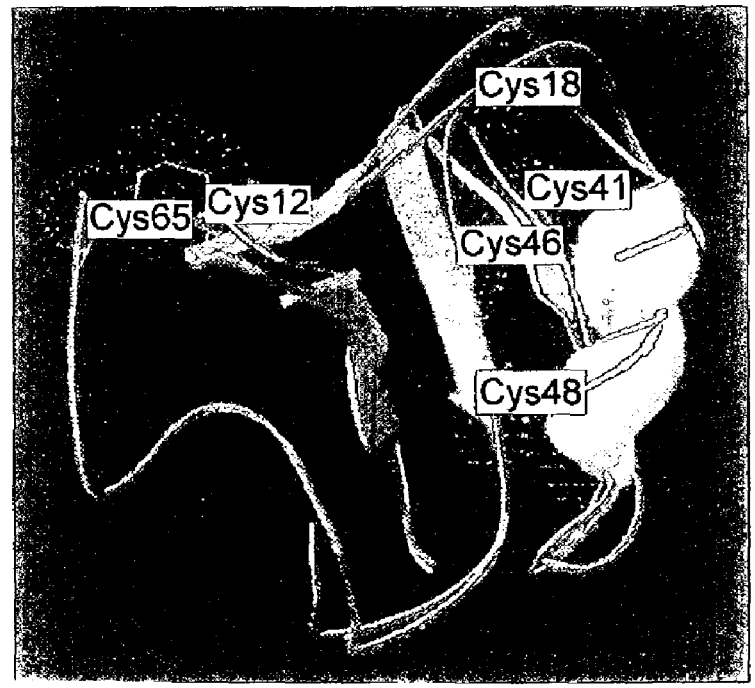

FIG. 4A and FIG. 4B. Molecular models of birtoxin. FIG. 4A shows the NMR resolved structure of CeNV 1. The disulfide bridge between residues Cys12 and Cys65 is the 'wrapper' disulfide. FIG. 4B shows the primary sequence of birtoxin overlaid and fitted onto the NMR structure of FIG. 4A. The disulfide bridge between Cys12–Cys65 in CeNV1 is absent in birtoxin.

Figure 5:
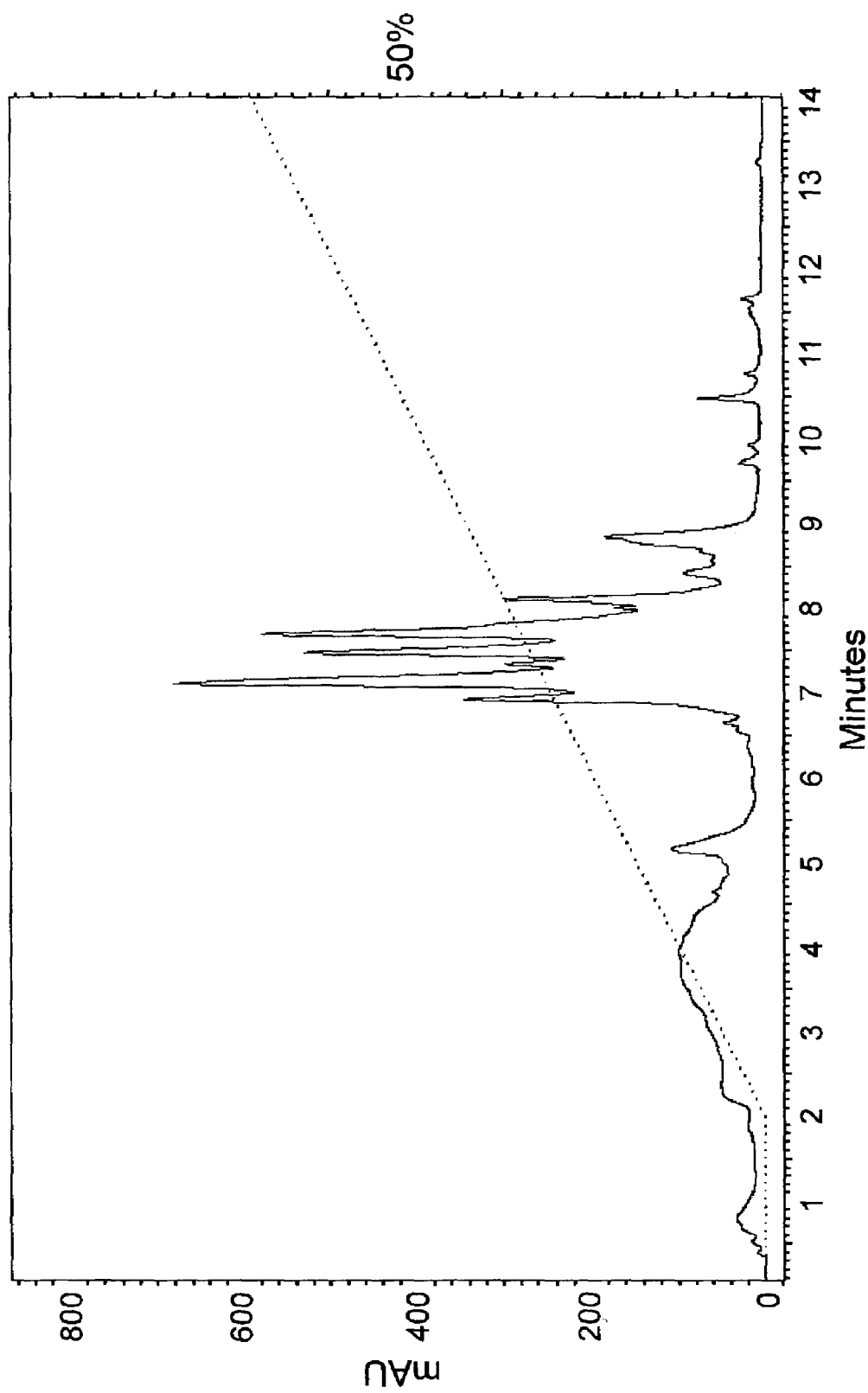

FIG. 5. UV trace of C4 separation of crude venom. Magic bullet C4 column has an equivalent resolving power to an analytical C4 column. Fractions P3 and P4 are well resolved using a C4 column. Fraction P3 contains ikitoxin and fraction P4 contains birtoxin. The dotted line represents the linear gradient of 2–65% solvent B.

Figure 6:
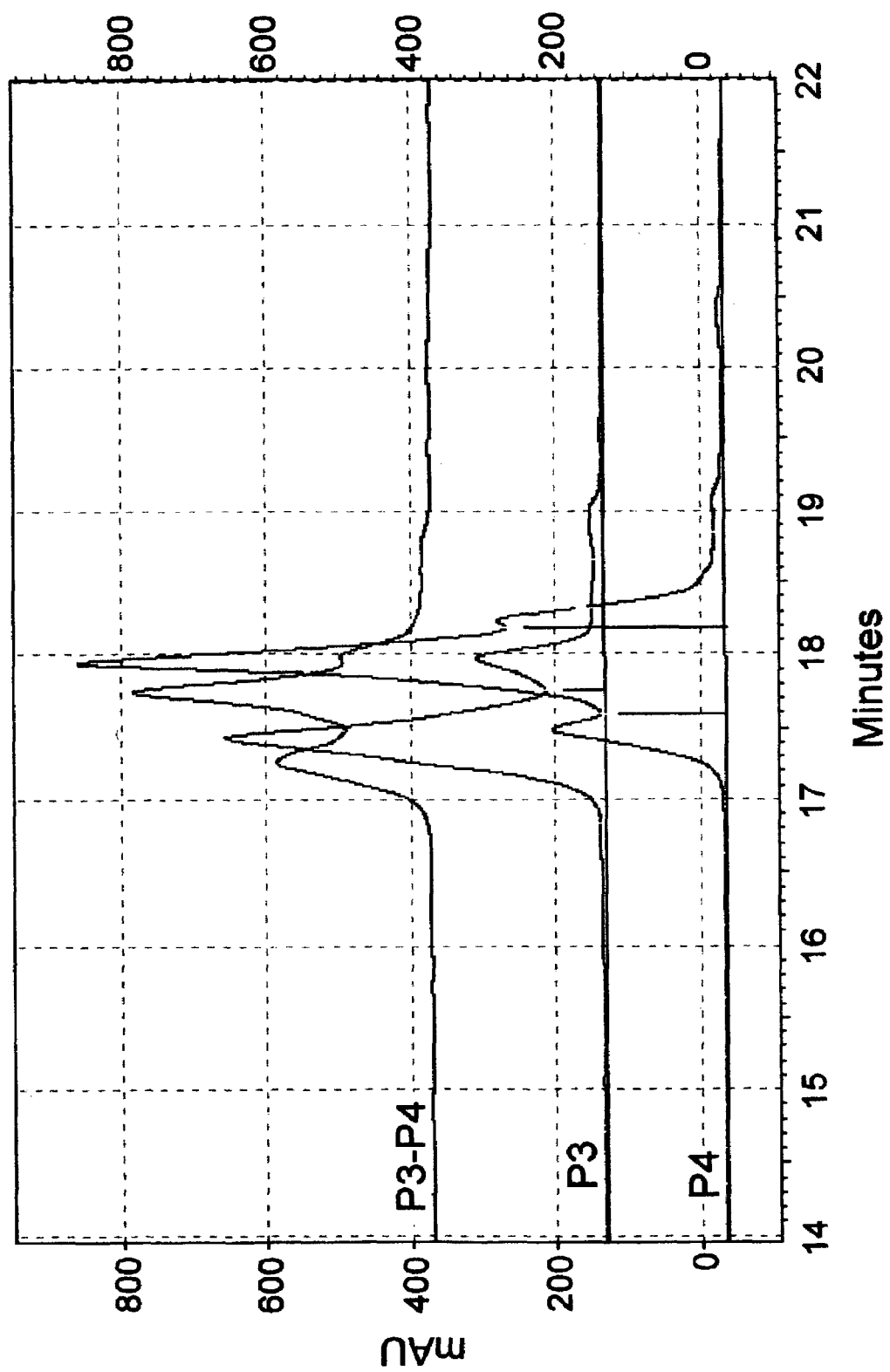

FIG. 6. C18 Microbore separation of (A) fraction P4 at the bottom, (B) fraction P3 in the middle and (C) a mixture of both fractions on the top. Note that ikitoxin resides in the interface of all three fractions.

Figure 7:
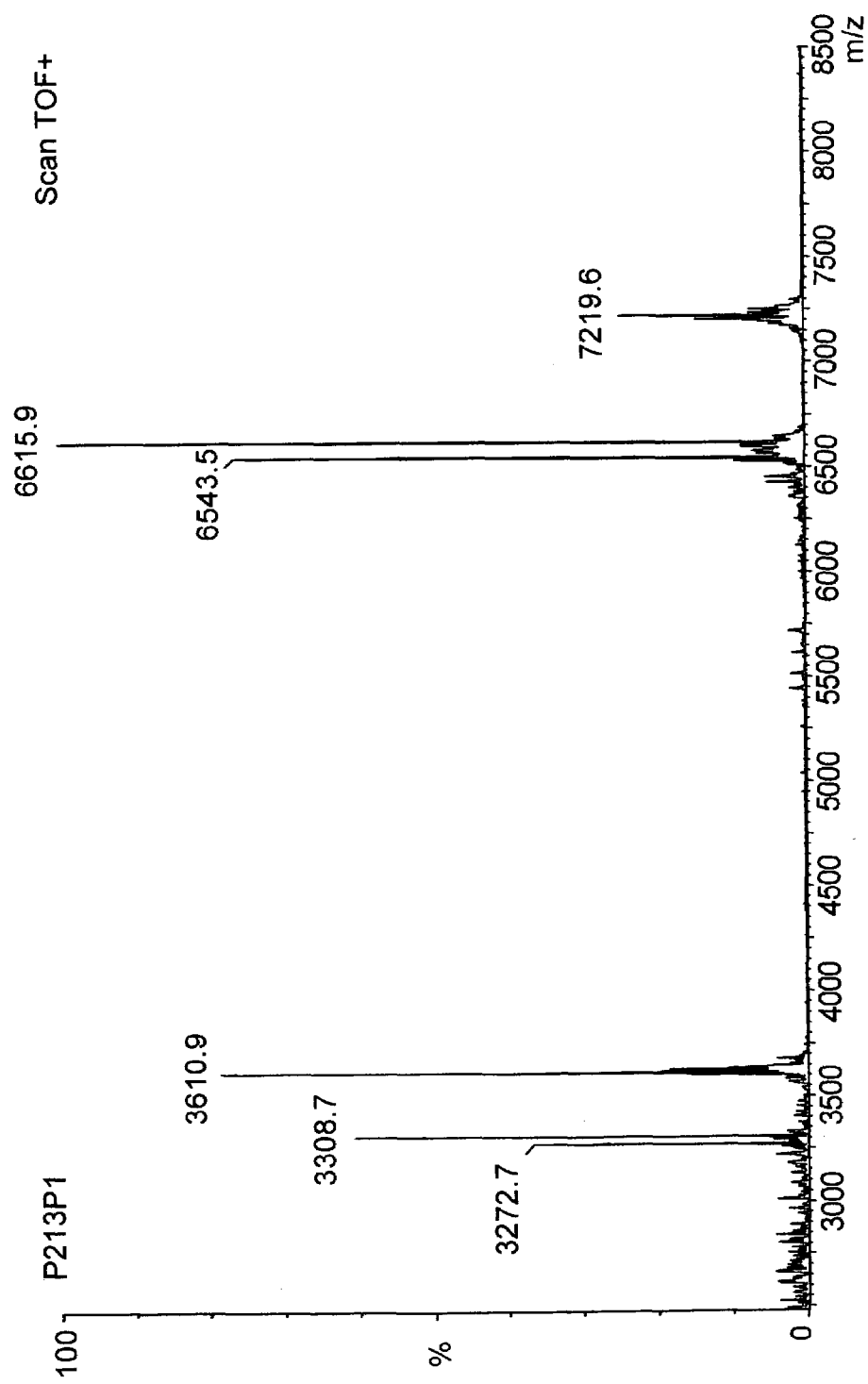

FIG. 7. Molecular mass of components in fraction P3 with corresponding $(M+H)^{+2}$ ions. Species 6543 is birtoxin $(M+H)^+$, species 6615 is ikitoxin $(M+H)^+$, species 7219 $(M+H)^+$ is uctoxin.

Figure 8B:
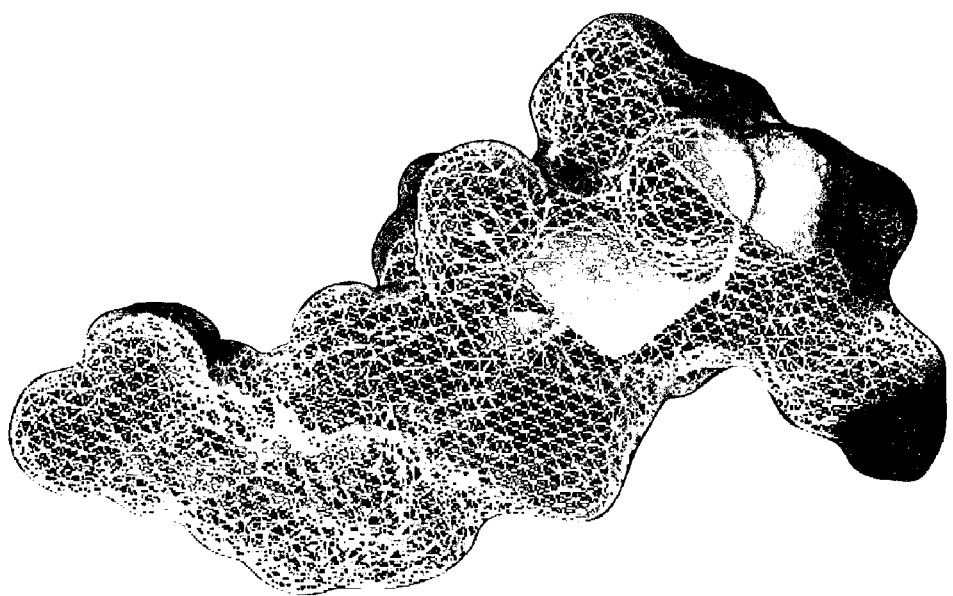
Figure 8A:
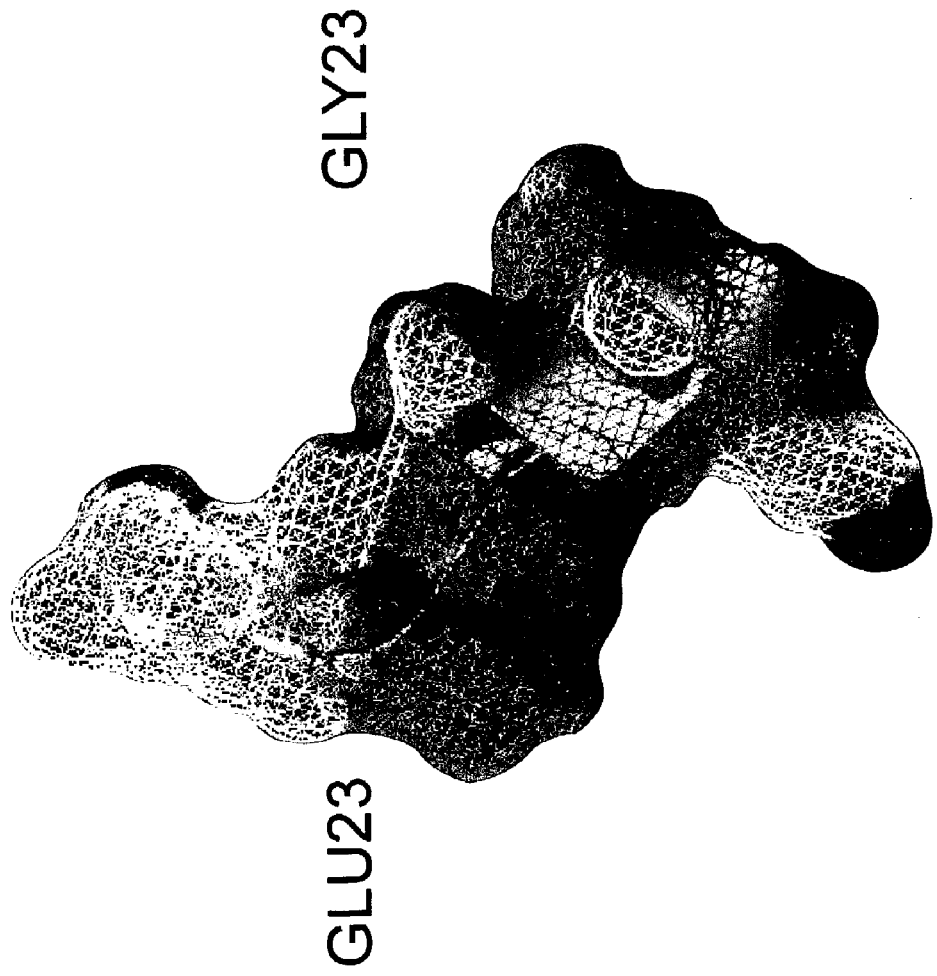

FIG. 8A and FIG. 8B. Molecular models of birtoxin and ikitoxin. FIG. 8A shows the model structure of birtoxin. FIG. 8B shows the model structure of ikitoxin. The alpha helix and preceding loop of both toxins were modeled based on the NMR structure of CeNV1. Surface potential calculation of the two models reveal that the GLU23 in ikitoxin increases the charge of the region.

Figure 9:
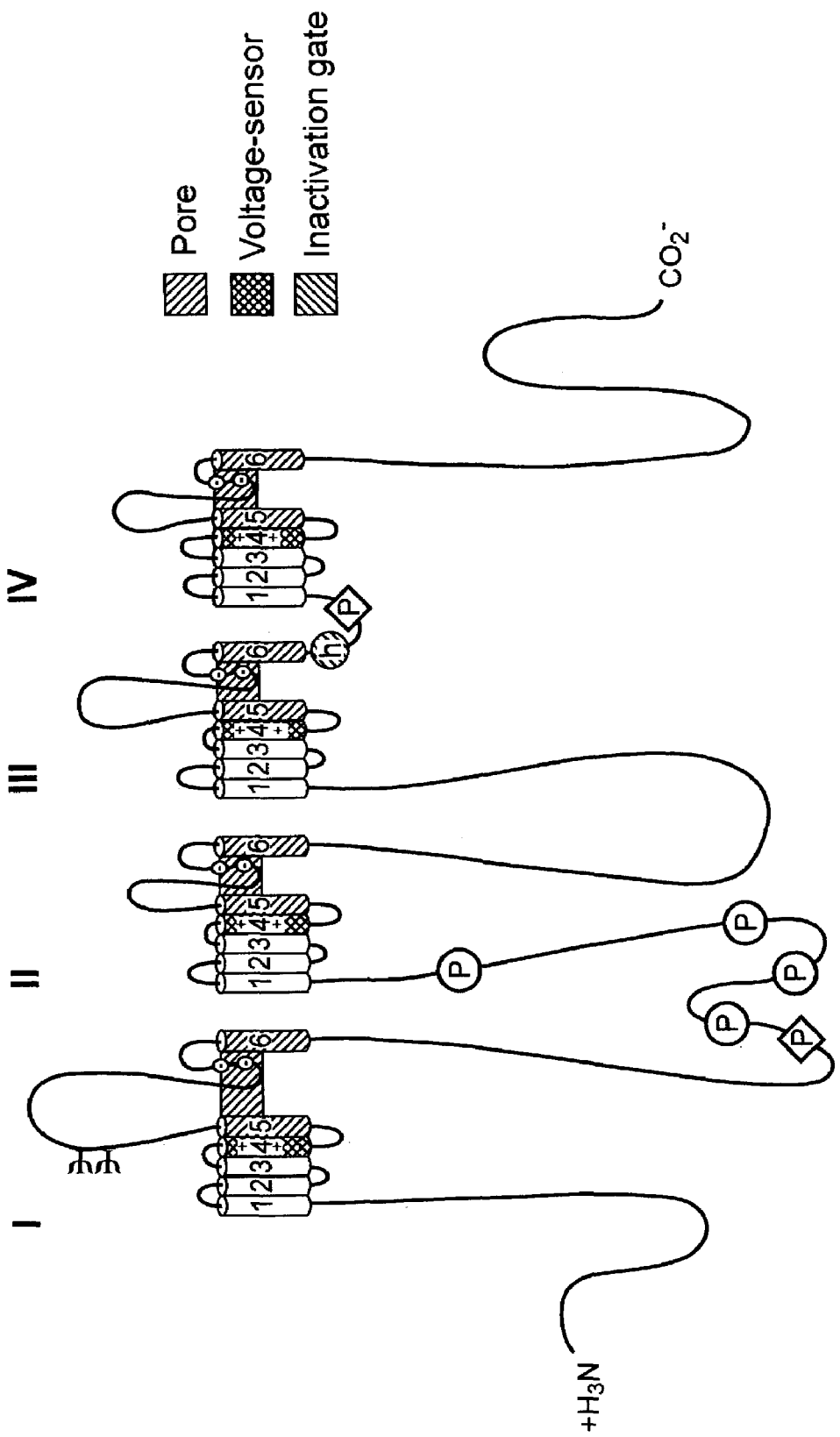

FIG. 9. Schematic of a voltage-gated sodium channel.

Figure 10:
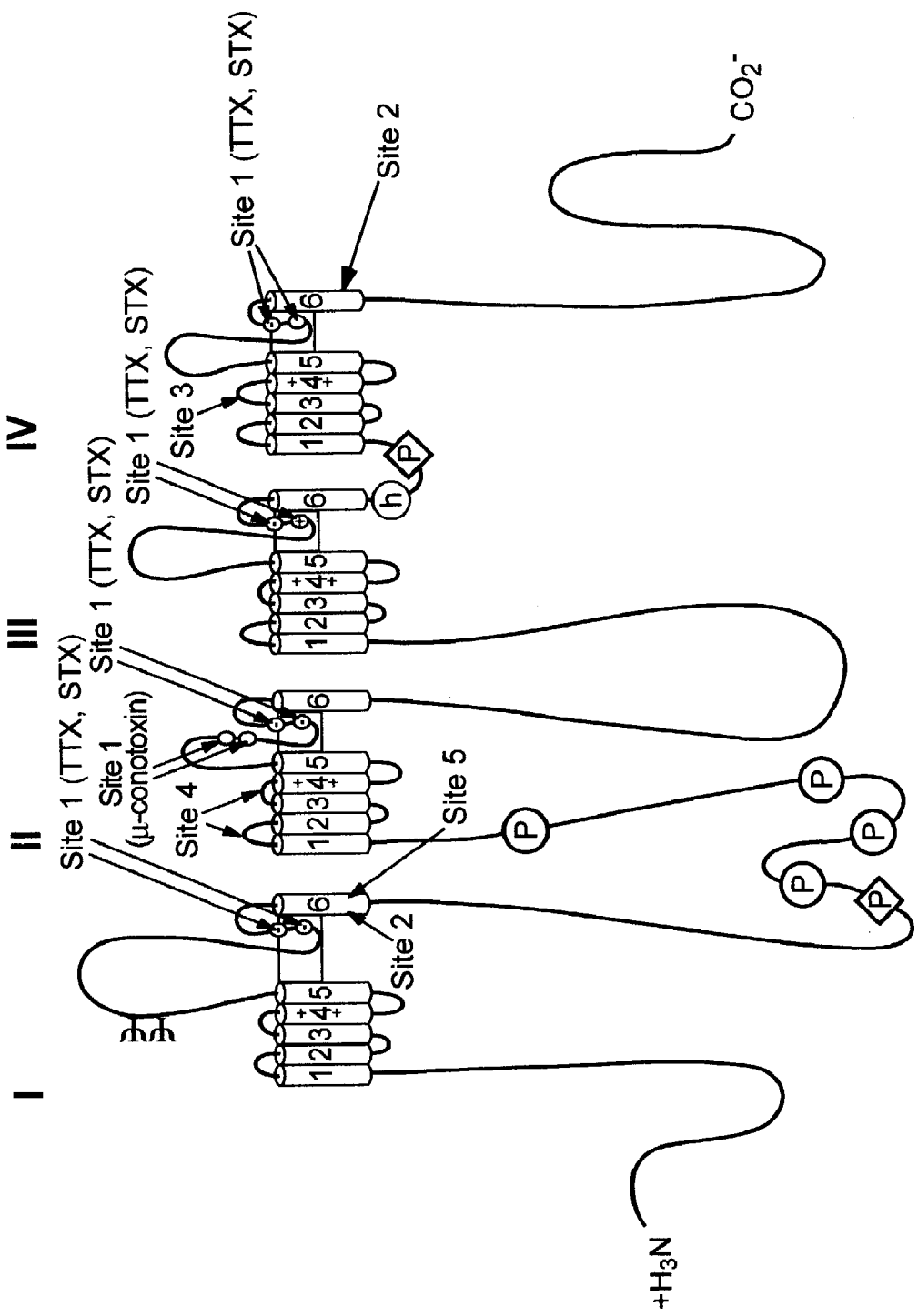

FIG. 10. Schematic of a voltage-gated sodium channel.

FIG. 11. Graph depicting the enhancement of $[^3H]$ binding to rat brain synaptosomes by birtoxin.

FIG. 12. Graph depicting the enhancement of $[^3H]$ binding to rat brain synaptosomes by uctoxin.

FIG. 13. Amino acid sequence alignment comparison of known polypeptides with parakinin-1 and parakinin-2. Primary sequences of parakinin-1 and parakinin-2 (SEQ ID NOS: 27 and 29) were aligned with known bradykinin-like using ClustalW program and visualized using the EsPriPt tool. Known bradykinin-like peptides used in the comparison and percent identities with bradykinin-like were as follows: Lysyl-bradykinin-like (Oncorhynchus mykiss; rainbow trout), Bradykinin-like (human), Waspkinin (Parapolybia indica; wasp), Megascoliakinin (Megascolia maculata), Thr6_bradykinin (Rana rugosa), Vespulakinin (Vespula maculafrons; eastern yellow jacket wasp), Maximakinin (Bombina maxima), Bradykinin (human), Each of the bradykinin-like peptides shows no more than 50% identity with the parakinin-1 and parakinin-2 polypeptides. The parakinin-1 and parakinin-2 peptides are 87.5% identical to each other, and are modified at the N-terminus. The alignment allowed the construction of consensus sequences, where the uppercase letters P and R represent invariant amino acids. Peptides are represented by standard single letter amino acid codes.

DETAILED DESCRIPTION OF THE INVENTION

Before the present venom sequences, compositions, and methods of preparing them are described, it is to be understood that this invention is not limited to particular toxin sequences, compositions, and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an antibody" includes a plurality of such antibodies and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

"Subjects" or "patients" as used herein, encompasses any subject or patient amenable to application of the methods of the invention, e.g., diagnostic methods., Mammalian subjects and patients, particularly human subjects or patients, are of particular interest.

As used herein, the terms "treatment," "treating," and the like, refer to obtaining a desired pharmacologic and/or physiologic effect. The effect may be prophylactic in terms of completely or partially preventing a symptom thereof and/or may be therapeutic in terms of a partial or complete cure for an adverse affect attributable to the condition. "Treatment," as used herein, covers any treatment of an injury in a mammal, particularly in a human, and includes: (a) preventing the injury, arresting any complications, and minimizing its effects; (b) relieving the symptoms; (c) preventing the disease from occurring in a subject which may be predisposed to the disease but has not yet been diagnosed as having it; (d) inhibiting the disease, i.e., arresting its development; and (e) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

The term "effective amount" or "therapeutically effective amount" means a dosage sufficient to provide treatment of the disease state being treated or to otherwise provide a desired pharmacologic and/or physiologic effect. The precise dosage will vary according to a variety of factors such as subject-dependent variables (e.g., age, immune system health, etc.), the cause of the injury (e.g., the species of scorpion), the disease (e.g., the nature of the effect on ion channels caused by the disease), and the treatment being effected. In the case of a scorpion sting, an "effective amount" is that amount necessary to substantially improve the likelihood of treating the sting, in particular that amount which improves the likelihood of successfully preventing effects of the toxins on the subject, relieving or minimizing toxin effects, or arresting any complications caused or exacerbated by the toxin. Where the a scorpion toxin is used as an insecticide or pesticide, an "effective amount" is that amount necessary to kill the insect or pest, or otherwise effect the behavior of the insect or pest in such a way that it no longer performs or causes undesired events or activities, e.g. consume or damage plants.

"Polynucleotide" and "nucleic acid" as used interchangeably herein refer to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" or "nucleic acid" is used to refer to a specific polynucleotide sequence (e.g. encoding a scorpion toxin), the terms are meant to encompass polynucleotides that encode a polypeptide that is functionally equivalent to the recited polypeptide, e.g., polynucleotides that are degenerate variants, or polynucleotides that encode biologically active variants or fragments of the recited polypeptide.

By "antisense polynucleotide" is meant a polynucleotide having a nucleotide sequence complementary to a given polynucleotide sequence including polynucleotide sequences associated with the transcription or translation of the given polynucleotide sequence (e.g., a promoter), where the antisense polynucleotide is capable of hybridizing to a polynucleotide sequence. Of particular interest are antisense polynucleotides capable of inhibiting transcription and/or translation, either in vitro or in vivo.

"Polypeptide" as used herein refers to an oligopeptide, peptide, modified polypeptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but is meant to encompass analogues, degenerate substitutions, etc.

The term "biologically active" refers to scorpion venom toxin polypeptides having structural, regulatory, or biochemical functions of a naturally occurring polypeptide. Likewise, "immunologically active" defines the capability of the natural, recombinant or synthetic scorpion toxin, or any oligopeptide thereof, to induce a specific immune response in appropriate animals or cells and to bind with specific antibodies.

The term "derivative" as used herein refers to the chemical modification of a scorpion toxin polypeptide. Illustrative of such modifications would be replacement of hydrogen by an alkyl, acyl, or amino group. A polypeptide derivative would retain essential biological characteristics of a natural polypeptide.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

The term "antibody" includes complete antibodies, as well as fragments thereof (e.g., F(ab')2, Fab, etc.) and modified antibodies produced therefrom (e.g., antibodies modified through chemical, biochemical, or recombinant DNA methodologies), with the proviso that the antibody fragments and modified antibodies retain antigen binding characteristics sufficiently similar to the starting antibody so as to provide for specific detection of antigen.

By "neurotoxin" is meant a poisonous complex, especially of protein, that acts on the nervous system.

By "envenomation" is meant when a subject is bitten or stung by a scorpion.

By "antivenom" is meant an antivenin or an antitoxin to a venom; or an antiserum containing such antitoxin.

By "bradykinin-like", "kinin-like" and "kinin" is meant a molecule with substantial sequence identity with human bradykinin, as shown on FIG. 1. "Parakinin" refer to the scorpion kinin-like molecules of the invention, as exemplified in FIG. 13. Parakinin and bradykinin are types of kinin.

By "scorpion toxins", "scorpion venom toxin" or "scorpion venom toxin polypeptide" is meant physiologically active peptides or peptide derivatives that have similarity to those isolated from scorpion venom. Examples of scorpion toxins include kinin-like polypeptides, as exemplified in FIG. 13, and birtoxins polypeptides, as described below. "Scorpion toxin family", "birtoxin family polypeptides" and "bradykinin family polypeptides" describes groups of birtoxin and bradykinin polypeptides, as described below. As such, the phrase "scorpion toxins" and the like does not necessarily limited the invention to molecules that are toxins from, or derived from, scorpions.

Isolation and Characterization of Scorpion Venom Toxins

The invention provides isolated polypeptides from the venom of the scorpion *P. transvaalicus*. The invention also provides novel scorpion antivenom compositions derived from such polypeptides, as well as methods for isolating the polypeptides and preparing scorpion antivenom compositions. The isolated polypeptides can be used to produce pharmaceutical compositions useful for treating diseases and conditions associated with ion channel function or kinin activity.

The venom of the South African Scorpion *Parabuthus transvaalicus* was characterized using a combination of mass spectrometry, reverse phase HPLC separation and bioassays. The crude venom was initially separated into ten fractions. Each purification step was followed by bioassays and mass spectroscopy. First, a C4 RP-HPLC column was used, then a C18 RP Microbore column purification resulted in >95% purity in the case of birtoxin, from a starting material of 230 μg of crude venom. About 12–14% of the $OD_{214}$ absorbance of the total venom as observed after the first chromatography step was composed of birtoxin, a novel moderately toxic, but very high abundance peptide of 58 amino acid residues. This peptide was lethal to mice at low microgram quantities and induced serious symptoms, including tremors, which lasted up to 24 hours post injection at submicrogram amounts. Additional studies of Birtoxin revealed that the toxin binds to sodium channel binding site 3 and blocks the sodium channel by prolonging the inactivation (preventing the closure of the channel) of the channel.

Another peptide isolated from the venom, ikitoxin, induced periodic unprovoked jumps in injected mice. Ikitoxin injected mice did not show any tremors or any of the symptoms of birtoxin. Ikitoxin is a 58 amino acid residue toxin that differs from birtoxin at only the $23^{rd}$ residue: in birtoxin the residue is glycine, in ikitixon it is glutamic acid. At least seven other fractions were identified that showed different activities, including one fraction with specificity against blowfly larvae. Subsequently, three additional toxins were purified and sequences were determined: both dortoxin and bestoxin were determined to have 58 amino acids, with a two amino acid difference of Lys20 in dortoxin to Glu20 in bestoxin and Glu45 in dortoxin to Ser45 in bestoxin; and uctoxin has been partially sequenced with 43 amino acids identified.

The birtoxin family toxins, being 50–60 residues long, are not part of the 60–70 residue 'Long Chain Neurotoxin' peptide family (Possani et al. (1999) *Eur. J. Biochem.* 264:287–300; Lebreton et al. (1994) *Biochemistry* 33:11135–11149; Syed et al. (1998) *Comp. Biochem. Physiol.* 121:323–332; and Gordon et al. (1998) *J. Toxicol. Tox.* Rev. 17:131–159). Furthermore, members of this long-chain family of peptides are known to contain 8 cysteine residues and four disulfide bridges. The second family of scorpion toxins is the 'Short Chain Neurotoxins' that are 30–40 residue long peptides with 6 or 8 cysteine residues. Birtoxin family polypeptides, having from about 50 to about 60 amino acids, and three disulfide bridges and six cysteine residues, bridge the gap between these two distinct groups, perhaps as an evolutionary link.

The 3D structure of birtoxin was further analyzed for similarity to the structure of closely related toxin peptides from *Centruroides exelicauda, Centruroides sculpturatus* and *Centruroides noxius* (Lee et al. (1994) *Biochemistry* 33:2468–2475; Jablonsky et al. (1995) *J. Mol. Biol.* 248: 449–458; Pintar et al. (1999) *J. Mol. Biol.* 287:359–367) and the primary sequence on these structures was overlaid. Primary structure and secondary structure prediction imply a similar general structure to known scorpion peptide toxins with the cysteine-stabilized α-helical motif, which involves a Cys-X—X—X-Cys stretch of the α-helix bonded through two disulfide bridges to a Cys-X-Cys triplet in a β-strand belonging to an anti-parallel β-sheet (Kobayashi et al. (1991) *Biopolymers* 31:1213–1220) despite the absence of the fourth disulfide bridge.

As confirmed with X-ray crystal structures and NMR studies, all known toxins in the Long Chain Neurotoxin family have four disulfide bridges. Three of these constitute the core of the structure, two disulfides bonding the α-helix to the anti-parallel β-sheet and a third disulfide links the β-sheet to an extended segment preceding the helix (Drakopoulou et al. (1998) *Biochemistry* 37:1292–1301; Carlier et al. (2000) *J. Peptide Res.* 55:419–427). Typically the fourth disulfide cross-links the first and last cysteine residues. Due to its position, this disulfide bridge is named the 'wrapper' disulfide bridge. This wrapper disulfide bridge is believed to be important for the peptide conformation and functionality. As seen in FIG. 4, the N and C termini of birtoxin are in close proximity, which would allow multiple hydrogen bonding between the N and the C terminal residues to hold the peptide's conformation similar to other toxins with four disulfide bridges since birtoxin lacks the wrapper disulfide bridge.

The biological activity of most neurotoxic peptides have been attributed to the C-terminal domain (Martin et al. (1989) in: Second Forum on Peptides (Aubry, A. et al., eds.) Vol 174, pp. 483–486, Colloque INSERM/John Libbey Eurotext Ltd.). The primary structure of birtoxin reveals that this toxin is slightly shorter than usual long chain neurotoxins (FIG. 4) and does not possess the amino acid residues that are suggested to be involved either in spatial arrangement of the molecule or in the binding of the molecule to the target ionic channels. Another interesting feature at the N-terminus of birtoxin is the presence of two proline residues separated by three amino acids, which might cause the N-termini to have a double turn (FIG. 4). This possible double turn motif has not been observed at the N-termini of scorpion toxins previously.

Thus, the results show birtoxin family polypeptides to be a novel structural alternative to the fourth disulfide bridge that is unique for birtoxin family toxins. Thus, birtoxin has a novel structural organization and an alternative system for keeping the polypeptide chain in a particular three-dimensional conformation that retains biological activity without the fourth disulfide bridge.

Two peptides, parakinin-1 of 986 Da and parakinin-2 of 972 Da, from *P. transvaalicus* were purified and sequenced. The amino acid sequences of the peptides are provided as SEQ ID NO:27 and SEQ ID NO:29, respectively. Variants of the two peptides in which the N-terminal Pro residue is a modified proline residue are described in SEQ ID NO:28, and SEQ ID NO:30, respectively. FIG. 13 shows a sequence alignment of the two toxins, parakinin1 (para1) and parakinin2 (para2) and other known parakinin-like peptides.

The peptides are each of 8 amino acids in length and are thus small compared to other scorpion venom polypeptides, which typically range from 3000 Da (i.e. approximately 30 residues) to 10000 Da (approximately 100 residues) in size. Both peptides are similar: they only differ at the 3$^{rd}$ amino acid position. As such, parakinin1 has a isoleucine at this position whereas parakinin 2 has a valine. Isoleucine and valine are "conserved" amino acids, meaning that they are similar in structure. A particular advantage of these polypeptides is that they are small, and, as such, are very easy to chemically synthesize on an industrial scale.

A portion of each of the parakinins (i.e. parakinin1 and parakinin2) has a unique modification at the N-terminus consisting of a modified proline residue. This unique modification of the N-terminal proline is unique among the members of the bradykinin-like family and can increase their stability in vivo, and hence their activity or potency.

Multiple sequence alignments of parakinin-like peptide sequences with sequences of other kinins reveals a consensus sequence for parakinin-like peptides. As such, peptides containing the sequence $X_1(X_2)_nX_3X_4X_5X_6PX_7R$ where $X_1$ is N-terminal and is a modified amino acid, usually modified Pro or modified Ser and more usually modified Pro, $(X_2)_n$ is contiguous sequence of any amino acids of length n, where n can be up to about 50, up to about 30, up to about 10 amino acids or 0 amino acids (i.e. $X_1$ is directly adjacent to $X_2$), $X_3$ is any amino acid, preferably Pro or Phe, $X_4$ is Ile, Leu or Val, preferably Ile or Val, $X_5$ is any amino acid, preferably Val, Ile, or Leu $X_6$ is any amino acid, preferably Ser, Thr or Pro, P is Pro, and $X_7$ is any amino acid, preferably Phe, Leu or Arg and R is Arg are encompassed by the invention. In some embodiments, the R (Arg) of this consensus sequence is C-terminal and in other embodiments, this R may not be present in the polypeptide and the polypeptide terminates at the $X_7$ residue.

Parakinin-like peptides may also include the consensus sequence $X_1X_2X_3X_4X_5PX_6R$, where $X_1$ is a modified amino acid, usually modified Pro or modified Ser, preferably Pro and may be N-terminal, $X_2$ is any amino acid, preferably Pro or Phe, $X_3$ is Ile, Leu or Val, preferably Ile or Val, $X_4$ is any amino acid, preferably Val, Ile or Leu, $X_5$ is any amino acid, preferably Ser, Thr or Pro, and $X_6$ is any amino acid, preferably Phe, Leu or Arg. As such, any peptide comprising the eight residues $X_1X_2X_3X_4X_5PX_6R$, especially at the C-terminus of a longer polypeptide, based on the consensus analysis, is encompassed by the invention. In some embodiments, the R (Arg) of this consensus sequence is C-terminal and in other embodiments, this R may not be present in the polypeptide and the polypeptide terminates at the $X_7$ residue.

By "modified", in relation to an N-terminal amino acid residue, is meant any modification at the N-terminal amino acid residue that blocks sequencing by the standard Edman degradation method. Such modifications include, but are not limited to acetylation, amidation, beta-methylthiolation, biotin, carbamylation, citrullination, c-mannosylation, deamidation, n-acyl diglyceride cysteine (tripalmitate), dimethylation, fad, farnesylation, formylation, geranyl-geranyl, gamma-carboxyglutamic acid, o-glcnac, glucosylation (glycation), hydroxylation lipoyl, methylation, myristoylation, palmitoylation, phosphorylation, pyridoxal phosphate, phosphopantetheine, pyrrolidone carboxylic acid, sulfation and trimethylation. Modifications may be on the —$NH_2$ group or any other group of the terminal amino acid residue.

In many embodiments an N-terminal modification increases polypeptide stability in vivo, and hence the activity and efficacy of the polypeptide in its ability to modulate kinin responses.

Exemplary polypeptides of the invention have the amino acid sequences listed in table 4, where each of the polypeptides in table 4, are modified (denoted by m, in subscript) at the N-terminal residue.

TABLE 4

$K_m$RPPIWSPLR
$M_m$KRSRIPSPRR
$Q_m$ZKRPPLFSPFRK
RPPLFTPFRKA
RPPVFTPFR
$T_m$ATTRRRGRPPVFSPFR
$D_m$LPKINRKGPRPPIFSPFR
$R_m$PPIFSPFR
$P_m$FIVPPFR
$P_m$FVVPPFR
$S_m$RPPLWSPLR
$S_m$KRSRLPSPRR
$S_m$ZKRPPIFSPFRK
$P_m$PPLFTPFRKA
PPPIFTPFR
$T_m$ATTRRRGRPPIFSPFR
$D_m$LPKINRKGPRPPLFSPFR
$R_m$PPVFSPFR
$S_m$FIVPPFR
SFVVPPFR

Apart having a modified N-terminal P residue, further differences between the parakinins and other kinins are found at positions 2 of the parakinin sequence, where Phe is found instead of a Pro; at position 3, where hydrophobic aliphatic residues (Ile and Val) are found instead of Gly; and at position 5, where a Pro is found instead of an acidic residue. As such, any polypeptide comprising the motif $PX_1X_2X_3PPFR$, where $X_1$ is any amino acid; $X_2$ is a hydrophobic aliphatic residue (i.e. Ala, Val, Ile, Leu; but not Gly) and $X_3$ is also a hydrophobic aliphatic residue, and P, F and R are standard single letter amino acid codes, is taught by the invention.

In describing parakinins, because of the parallels of their structure and function with bradykinin, it is understood that they may be product of cleavage of a larger polypeptide, pro-parakinin. As such, pro-parakinins can be defined by any of the above sequence identifiers.

In a further embodiment of the invention where a kinin antagonist is desired, any of the above polypeptides described by the sequences PFIVPPFR and PFVVPPFR and consensus sequences rppgXXPfR, $X_1X_2X_3X_4X_5PX_6R$, $X_1(X_2)_nX_3X_4X_5X_6PX_7R$ and $PX_1X_2X_3PPFR$, where P, F, I, V and R represent single letter amino acid codes, where the N-terminal amino acid residue is modified and the P at the position third from the C-terminal end of these consensus motifs (i.e. the P of PfR in rppgXXPfR or the P of $PX_6R$ in $X_1X_2X_3X_4X_5PX_6R$, etc.) is substituted with the amino acids described in U.S. Pat. No. 4,801,613, for example an aromatic amino acid of the D-configuration, the peptide is a kinin antagonist. Further exemplary modifications that can be used to create kinin antagonists are described in Kotovych et al (Biochem Cell Biol, 76: 257–266 1988), the disclosure of which is hereby incorporated by reference). Antagonists or agonists may be used to inhibit or activate, respectively, the bradykinin B1, B2 or both the B1 and B2 receptors, as described in Hall et al (Gen. Pharmac. 28:1–6 1997) and Campbell (Clin. Exp. Pharm. Phys. 28:1060–1065).

It is understood that because of the size of these polypeptides and their ease of chemical synthesis, the peptides are not necessarily limited to those made using D- or L- amino acids.

Peptide toxins from scorpions have several major applications. First, the potent peptides can be employed in the design and production of superior antivenom compositions. Birtoxin peptides from scorpions may be used as probes for identifying distinct types of ion channels and are important tools for understanding their physiology (Becerril et al. (1997) Toxicon 35:821–835; Froy et al. (2000) Pest. Manag. Sci. 56:472–474); parakinins, likewise, may be used as tools for modulating and understanding pain and inflammatory responses. Furthermore, many neurotoxins derived from venom and other sources can be used to treat various disorders. For example, botulinum toxin, which is responsible for many lethal cases of food poisoning, is currently used by local injection to paralyze muscle cells in patients suffering from muscle spasms. Neurotoxins are also interesting for research in drug discoveries because many act selectively on particular cells or pathways. An example of a drug developed from a snake venom is the inhibitor of angiotensin-converting enzyme (ACE). The enzyme converts an inactive precursor into the hormone angiotensin, which causes blood vessels to constrict and thus raises the blood pressure in a subject. As a result, ACE inhibitors, by blocking the activity of the enzyme, have the ability to lower blood pressure. These drugs, which are sold as captopril, enalapril, among others, are some of the most prescribed medicines in the world. Finally, neurotoxins derived from scorpion venom can be used for insecticide and/or pesticide activities, where the neurotoxin acts selectively on insects in general or on certain species of insects or pests such as rodents, e.g. mice or rats.

By understanding the structural features of a particular scorpion toxins, such as members of birtoxin family polypeptides (e.g., birtoxin, ikitoxin, dortoxin, bestoxin, and the like) or parakinin family polypeptides (e.g. parakinin-1 and parakinin-2 and the like), it will be possible to design drugs that mimic the active sites of the scorpion toxin. For example, if a particular neurotoxin blocks neuronal potassium channels, this may provide a blueprint for designing a new drug to treat Alzheimer's disease. Furthermore, neurotoxins that act as activators of the neuronal potassium channels could be used to treat epilepsy, or increase the permeability of the blood brain barrier. Of particular interest are modified scorpion venom toxins that antagonistic to particular ion channels or kinin receptors. Such drugs may be used, for example, to block pain or inflammation in a disease or condition where bradykinins, parakinins, or kinins are released.

Ion Channels

Ion channels are proteins that span cell membranes providing pathways for the flow of ions such as chloride, sodium, calcium, or potassium. These channel proteins are involved in many cellular functions such as nerve signaling, muscle contraction and hormone secretion. Over the past several years there has been an explosive growth in the number of cloned and expressed ion channels, as well as in discoveries which link channels to disease. Moreover, now that it is clear that there are many subtypes of ion channels differentially distributed throughout the body, the possibilities for selective targeting of specific channels in specific tissues are unlimited. This selective targeting will reduce unwanted drug-related side effects and toxicities. Agents that modulate specific ion channels in specific tissues are expected to target select disease states without altering normal functions.

Various types of voltage-activated ion channels have now been cloned and functionally expressed. Sequence comparisons and hydropathy analyses have revealed a great deal of structural homology among these channels. Each channel sequence is composed of a repeating motif of transmembrane spanning domains that combine in various ways to form channels (For a review of the field, see Andersen and Koeppe, II, Physiological Reviews (1992) Vol. 72).

Site-directed mutagenesis has allowed researchers to probe the primary structure of ion channel proteins for critical amino acid residues involved in the binding sites of drug molecules. These studies will allow for the development of agents targeted for specific channel subtypes and binding sites. To date, several classes of ion channels, including potassium, sodium, and chloride, have received intensive characterization leading to a basis on which to consider structure-based drug design.

Potassium channels can be divided into at least 6 major classes, and 15 subclasses, each with its own distinct biophysical and pharmacological identity. Potassium channels are largely responsible for maintenance functions like establishing the membrane potential in unstimulated cells, or in switching on, or off, a cell's electrical activity. Thus, these channels in part control the cell's capacity for nervous transmission, muscle contraction and secretion. Due to their integral roles in almost all normal signal processing, agents that modulate potassium channels are likely to be useful for treating conditions such as diabetes and muscular sclerosis, cardiac arrhythmias and vascular hyperactivity.

Voltage gated sodium channels play a fundamental role in excitable cells. Therefore, Voltage-gated sodium channels are crucial for cardiac and nerve function, since the action potential of nerves and muscle cannot occur without them. They mediate an increase in Na+ ion permeability, thereby transmitting depolarizing impulses rapidly throughout cells and cell networks. Sodium channels are known to be involved in pathophysiological processes such as ischaemia, epilepsy and chronic pain. The sodium channel is composed of three polypeptide subunits, often as $\alpha$, $\beta_1$, $\beta_2$, heterotrimer. Toxin binding sites are generally located on the a subunit which consists of four homologous domains (I–IV) each of 300–200 amino acids and containing six transmembrane helices (S1–S6) that associate to form a barrel like structure around the fourth of the six helices (See FIGS. 9 and 10) (see Rogers and Catterall (1996) *J. Biol. Chem.* 271:15950–15962). The fourth helix is relatively charged, and it is thought that this is the 'chemosensory' part of the channel, changing conformationally in response to changes in electric field regulating the influx of sodium into the cell.

Sodium channels are modulated by a wide variety of toxins, which bind to various sites at the channel polypeptide (Catterall (1992) *Physiol. Rev.* 72:15–48). The $\alpha$-toxins from scorpions are known to bind to receptor site 3 (Catterall (1992) *Physiol. Rev.* 72:15–48), which is formed by amino acid residues in the extracellular linker between segments S3 and S4 in the fourth homologous domain of (D4) of the channel polypeptide (Rogers et al. (1996)*J. Biol. Chem.* 271:15950–15962). The extracellular regions between segments S5 and S6 in domains D1 and D4 also contribute to receptor site 3 (Thomsen and Catterall (1989) *Proc. Natl. Acad. Sci. USA* 86:10161–10165). The major functional effect of scorpion $\alpha$-toxins on voltage-gated sodium channels is a marked slowing of fast inactivation. The binding of scorpion $\alpha$-toxins to mammalian sodium channels has been shown to be voltage dependent in a sense that the affinity decreases with membrane depolarization. Hence, receptor site 3 was suggested to undergo conformational change during depolarization, leading to decreased affinity to the toxin (Catterall (1977) *J. Biol. Chem.* 252:8660–8668; Catterall (1992) *Physiol. Rev.* 72:15–48).

Different scorpion $\alpha$-toxins have been shown to be active on sodium channels in various excitable cells (Gordon et al. (1998) *Toxicol. Toxon. Rev.* 17:131–159). Recently, the class of scorpion $\alpha$-toxins has been subdivided into three major groups according to their activated and properties of binding to voltage-gated sodium channels in mammals and insects (Gordon et al. (1998) *Toxicol. Toxon. Rev.* 17:131–159). The classic $\alpha$-toxins are highly active in mammals, $\alpha$-toxins, highly active in insects form the second group, and the third group comprises the so-called $\alpha$-like toxins, which are highly active in insects and mammals.

Bradykinin

It has been reported that the half life of bradykinin in the systemic circulation is less than 30 seconds, and bradykinin appears to be completely (i.e. 98%–99%) destroyed on a single passage through the pulmonary circulation as determined in an anesthetized rat by measuring the depressor effects of an agonist following intra-aortic and intravenous administration. Resistance of bradykinin agonists to pulmonary kininase destruction in vivo also appears to be promoted by addition of single (i.e. D-Arg-, D-Lys-, Lys-) and double (D-Lys-Lys) basic amino acid residues to the N-terminal of the bradykinin sequence. The addition of the dipeptide Lys-Lys to the N-terminus of bradykinin agonists has been reported to confer complete resistance to in vivo destruction on initial passage through the pulmonary circulation. For this purpose, derivatives obtained by reduction of one of the amide linkage and other structures derived from bradykinin are proposed in U.S. Pat. Nos., 5,112,596 and 5,268,164 which relate their property of increasing the permeability of the blood-brain barrier; one of these compounds, RMP7, is currently undergoing a clinical trial in order to evaluate its ability to potentiate the action of anticancer drugs in patients from cerebral gliomas.

Several research groups have prepared bradykinin receptor antagonists. Stewart and Vavrek (U.S. Pat. No. 4,801,613) disclose a series of bradykinin antagonists wherein the L-Pro at position 7 of the peptide hormone is substituted with an aromatic amino acid of the D-configuration which converts bradykinin agonists into bradykinin antagonists. The analogs produced are useful in treating conditions and diseases of a mammal in which an excess of bradykinin or related kinins are induced or injected as by insect bites into the body.

Of especial interest are bradykinin-like molecules that have increased activity over the wild type bradykinin. Such molecules may be used, for example, to modulate the permeability of the blood-brain barrier.

Nucleic Acid Compositions

The nucleic acid compositions of the subject invention may encode all or part of the polypeptides of the subject invention, e.g. the nucleic acids may encode all or part of any one of SEQ ID NOS:1–5, 27–30, and may be synthesized oligonucleotides, mRNA, cDNA, or genomic DNA. These polynucleotides can be used, when in a recombinant expression vector, to produce the encoded scorpion venom toxins. They are also useful as hybridization probes in methods of detecting scorpion venom toxins gene expression, specifically transcription. Accordingly, the invention further provides recombinant vectors and host cells comprising scorpion toxin polynucleotides of the invention.

Novel polynucleotides of the invention comprise polynucleotides coding for a scorpion venom toxin polypeptide sequence set forth in any one of SEQ ID NOS:1–5, 27–30, or an identifying sequence thereof. An "identifying sequence" is a contiguous sequence of residues at least about 10 nucleotides (nt) to about 20 nt in length, usually at least about 40 nt to about 55 nt in length, that uniquely identifies the provided sequence. Encompassed in the term "scorpion venom toxin-encoding polynucleotide" are polynucleotides comprising about 10, 20, 25, 50, 75, 100, 125, or 150 contiguous nucleotides coding for any one of SEQ ID NOS:1–5, 27–30, including the entire coding region of SEQ ID NOS:1–5, 27–30. Polynucleotides comprising sequences which encode the region of the birtoxin family polypeptide that interacts with an ion channel are also of interest. Such fragments may be about 30 to 50 nucleotides in length, up to the complete sequence.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., Molecular Cloning: A Laboratory Manual, 2nd Ed. (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., supra, at page 9.50.

Variables to consider when performing, for example, a Southern blot are (1) the complexity of the DNA being blotted and (2) the homology between the target and the sequences being detected. The total amount of the polynucleotides to be studied can vary a magnitude of 10, from 0.1 to 1 µg for a plasmid or phage digest to $10^{-9}$ to $10^{-8}$ µg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 µg of yeast DNA, blotting for two hours, and hybridizing for 4–8 hours with a target polynucleotide radiolabeled with $10^8$ cpm/µg. For a single-copy mammalian gene a conservative approach would start with 10 µg of DNA, blot overnight, and hybridize overnight in the presence of 10% dextran sulfate using a target polynucleotide radiolabeled with greater than $10^8$ cpm/µg, resulting in an exposure time of ~24 hours.

Several factors can affect the melting temperature ($T_m$) of a DNA-DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a single equation:

$T_m=81+16.6(\log 10 Ci)+0.4[\%G+C]-0.6(\%formamide)-600/n-1.5(\% mismatch)$, where Ci is the salt concentration (monovalent ions) and n is the length of the hybrid in base pairs (slightly modified from Meinkoth and Wahl, (1984) *Anal. Biochem.* 138:267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of at least about 5×SSC at 65° C., or at least about 4×SSC at 42° C.; see, for example, U.S. Pat. No. 5,707,829, the disclosure of which is herein incorporated by reference.

Generally, hybridization is performed using at least 18 contiguous nucleotides of at least one of SEQ ID NOS:1–5, 27–30. That is, when at least 18 contiguous nucleotides of one of the disclosed SEQ ID NOS:1–5, 27–30 used as a probe, the probe will preferentially hybridize with a nucleic acid or mRNA comprising the complementary sequence, allowing the identification and retrieval of the nucleic acids of the biological material that uniquely hybridize to the selected probe. Probes of more than 18 nucleotides can be used, e.g. probes of from about 25 nucleotides to about 40 nucleotides, from about 50 nucleotides to about 75 nucleotides, up to the entire coding region can be used, but 18 nucleotides generally represents sufficient sequence for unique identification.

The nucleic acids of the invention also include naturally occurring variants of the nucleotide sequences, e.g. degenerate variants, allelic variants, etc. Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25–30% base pair mismatches relative to the selected nucleic acid probe. In general, allelic variants contain 15–25% base pair mismatches, and can contain as few as even 5–15%, or 2–5%, or 1–2% base pair mismatches, as well as a single base-pair mismatch.

Homologs of the scorpion venom toxins are also provided in the present invention. Such homologs can be identified by any of a number of methods known to those skilled in the art. A fragment of the provided nucleic acid may be used as a hybridization probe against a cDNA library from the target organism of interest, where low stringency conditions are used. The probe may be a large fragment, or one or more short degenerate primers.

The invention also encompasses homologs corresponding to the nucleic acids encoding any one of SEQ ID NOS:1–5, 27–30, where the source of homologous genes can be any related species within the same genus or group. Within a group, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared.

The term "birtoxin family polynucleotide" encompasses polynucleotides which encode a birtoxin family polypeptide, a fragment thereof, or a fusion protein thereof, as described above. Thus, in some embodiments, a birtoxin family polynucleotide comprises a nucleotide sequence encoding a polypeptide comprising at least about 5, 10, 15, 20, 25, 50, 75, 100, 125, or 150 of the sequence set forth in any one of SEQ ID NOS:1–5. In other embodiments, a birtoxin family polynucleotide comprises a nucleotide sequence encoding the entire polypeptide having the amino acid sequence set forth in any one of SEQ ID NOS:1–5, 27 and 29. In still other embodiments, a birtoxin family polynucleotide comprises a nucleotide sequence which encodes a polypeptide comprising an amino acid sequence sharing at least about 60%, preferably at least about 70%, more preferably at least about 80%, even more preferably at least about 87%, 90%, 95%, 98%, or 99% or more amino acid sequence identity with the sequence depicted in any one of SEQ ID NOS:1–5.

The term "parakinin polynucleotide" encompasses polynucleotides which encode a parakinin family polypeptide, a fragment thereof, or a fusion protein thereof, as described above. Thus, in some embodiments, a parakinin family polynucleotide comprises a nucleotide sequence encoding a polypeptide comprising at least about 5, 10, 15, 20, 25, 50, 75, 100, 125, or 150 of the sequence set forth in any one of SEQ ID NOS:27–30. In other embodiments, a parakinin family polynucleotide comprises a nucleotide sequence encoding the entire polypeptide having the amino acid sequence set forth in any one of SEQ ID NOS:27–30. In still other embodiments, a parakinin family polynucleotide comprises a nucleotide sequence which encodes a polypeptide comprising an amino acid sequence sharing at least about 60%, preferably at least about 70%, more preferably at least about 80%, even more preferably at least about 87%, 90%, 95%, 98%, or 99% or more amino acid sequence identity with the sequence depicted in any one of SEQ ID NOS:27–30.

As is known to one of skill in the art, using the standard genetic code table, a polynucleotide encoding a subject polypeptide can be designed and using a nucleic acid synthesizer or other means, a polynucleotide encoding a subject polypeptide may be produced.

Also encompassed by the invention are polynucleotides complementary to a birtoxin family polynucleotide, as defined above. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense polynucleotides, and methods of using such, are described in numerous publications, including, e.g., "Antisense Technology: A Practical Approach" Lichtenstein and Nellen, eds. (1997) IRL Press.

Antisense molecules can be used to down-regulate expression of scorpion venom toxin polypeptide genes in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by, reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 75, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, etc. may be used to inhibit gene expression. Ribozymes may be synthesized in vitro and administered, or may be encoded on an expression vector, from which the ribozyme is synthesized in the targeted cell (for example, see International patent application WO 9523225, and Beigelman et al.

(1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

A scorpion venom toxin-encoding polynucleotide may be a birtoxin family or parakinin family cDNA. The term "cDNA" as used herein is intended to include all nucleic acids that share the arrangement of sequence elements found in native mature mRNA species, where sequence elements are exons and 3" and 5" non-coding regions. Normally mRNA species have contiguous exons, with the intervening introns, when present, removed by nuclear RNA splicing, to create a continuous open reading frame encoding the protein protein.

Also encompassed by the term "scorpion toxin polynucleotide" are scorpion toxin genomic sequences. A genomic sequence of interest comprises the nucleic acid present between the initiation codon and the stop codon, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, up to about 6 kb, of flanking genomic DNA at either the 5' or 3' end of the transcribed region. The genomic DNA may be isolated as a fragment of 50 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for regulation in tissues where scorpion toxins polypeptide are expressed. The tissue specific expression is useful for determining the pattern of expression, and for providing promoters that mimic the native pattern of expression. Naturally occurring polymorphisms in the promoter region are useful for determining natural variations in expression.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1:194–205; Mortlock et al. (1996) *Genome Res.* 6:327–33; and Joulin and Richard-Foy (1995) *Eur. J. Biochem.* 232: 620–626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to one of the subject genes in order to promote expression of wild type or altered scorpion toxin polypeptide, or other proteins of interest in cultured cells.

The nucleic acid compositions of the subject invention may encode all or a part of the scorpion toxin polypeptides of the invention. Double or single stranded fragments of the DNA sequence may be obtained by chemically synthesizing oligonucleotides in accordance with conventional methods, by restriction enzyme digestion, by PCR amplification, etc For the most part, DNA fragments will be of at least 15 nt, usually at least 25 nt or 35 nt or 45 nt but may be as long as 50 nt, 60 nt, 70 nt, 80 nt, and even as long as 90 nt or 100 nt. Small DNA fragments are useful as primes for PCR, hybridization screening probes, etc. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The polynucleotides of the invention are isolated and obtained in substantial purity, generally as other than an intact chromosome. Usually, the DNA will be obtained substantially free of nucleic acid sequences other than a scorpion venom toxin-encoding polynucleotide, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of scorpion toxin gene expression in the sample.

The sequence of a scorpion venom toxin-encoding nucleic acid or gene, including any flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one amino acid, and may differ by at least one or two but not more than about ten amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al, *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques*

13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1990); and Zhu, *Anal Biochem* 177:120–4 (1989). Such mutated genes may be used to study structure-function relationships of birtoxin family polypeptides or to alter properties of the protein that affect its function or regulation.

Scorpion Venom Toxin Peptide Homologs

Homologs and orthologs of scorpion toxin polypeptides are identified by any of a number of methods. A fragment of scorpion venom toxin polynucleotide or cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Hybridization methods and conditions are well known in the art, see, e.g., U.S. Pat. No. 5,707,829. Nucleic acids having a region of substantial identity to a nucleic acid encoding a birtoxin family polypeptide, e.g. allelic variants, genetically altered versions of the gene, etc., bind to the scorpion venom toxin family polynucleotide sequence under stringent hybridization conditions. By using probes, particularly labeled probes of DNA sequences, one can isolate homologous or related genes. The source of homologous genes can be any species of scorpion or any other organism that produces neurotoxins, e.g., snakes, arachnids, lizards, sea anemones, and the like.

Between scorpion species, homologs have substantial sequence similarity, i.e. at least 75% sequence identity between nucleotide sequences, in some cases 80 or 90% sequence identity, and may be as high as 95%, 98%, or 99% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403–10.

Scorpion Toxin Family Polypeptides

The present invention provides isolated scorpion toxin polypeptides. The inventors have discovered novel families of toxic polypeptides in the venom of the scorpion *P. transvaalicus*. These polypeptides bind to and modulate the activity of ion channels or have kinin activity. Scorpion toxin polypeptides can be used to generate antibodies which specifically bind to scorpion toxin polypeptides. The scorpion toxin polypeptides are also useful in assay methods to identify agents which modulate birtoxin family polypeptide-ion channel binding, and/or modulate ion channel activity, or modulate kinin (e.g. bradykinin, parakinin and the like) activity.

The term "scorpion toxin family" encompasses scorpion toxin polypeptides from a variety of eukaryotic species, including, but not limited to, any species of scorpion, especially *P. transvaalicus*. Scorpion toxin family polypeptides may have from about 50 to about 60 amino acids, and three disulfide bridges and six cysteine residues. Known birtoxin family polypeptides include birtoxin, ikitoxin, bestoxin, and dortoxin. Also, as used herein, "scorpion toxin family" encompasses the novel *P. transvaalicus* toxin uctoxin, which has a high level of identity to known alpha toxins, including the presence of four conserved disulfide bridges. Scorpion toxin family polypeptides, may also be related to bradykinin, in that it shows sequence identity to bradykinin (see FIG. 13). In one embodiment, scorpion family polypeptides that are related to bradykinin have a modified N-terminal proline residue.

As used herein, "scorpion toxin polypeptide" refers to an amino acid sequence of a recombinant or non-recombinant polypeptide having an amino acid sequence of i) a native birtoxin or parakinin family polypeptide, ii) a fragment of a birtoxin or parakinin family polypeptide, iii) polypeptide analogs of a birtoxin of parakinin family polypeptide, iv) variants of a birtoxin or parakinin family polypeptide; v) an immunologically active fragment of a birtoxin or parakinin family polypeptide; and vi) fusion proteins comprising a birtoxin of parakinin family polypeptide. Birtoxin or parakinin family polypeptides of the invention can be obtained from a scorpion biological sample, or from any source whether natural, synthetic, semi-synthetic or recombinant.

"Scorpion venom toxin polypeptide" refers to the amino acid sequences of isolated scorpion toxin family polypeptides, and is meant to include all naturally-occurring allelic variants, and is not meant to limit the amino acid sequence to the complete, native amino acid sequence associated with the recited protein molecule. The term "scorpion toxin family polypeptide" encompasses an amino acid sequence encoded by an open reading frame (ORF) of a scorpion toxin family polynucleotide gene, including the full-length native polypeptide and fragments thereof, particularly biologically active fragments and/or fragments corresponding to functional domains, e.g., a ion channel-binding domain or region, etc., and including fusions of the subject polypeptides to other proteins or parts thereof.

Those skilled in the art will appreciate that changes can be made to scorpion toxin family polypeptide sequences, including the sequences depicted in SEQ ID NOS:1–5 and 27–30 without substantially affecting a function of the birtoxin family polypeptide. Thus, the term "birtoxin family polypeptide" encompasses polypeptides with conservative amino acid substitutions compared with the sequences depicted in SEQ ID NOS:1–5 and 27–30. Examples of conservative amino acid substitutions include Ser/Thr; Ala/Val; Leu/Ile; Asp/Glu; and Phe/Tyr. Clearly, other amino acid substitutions, deletions, and insertions can be made to the polypeptide without affecting one or more functions of the polypeptide. Those skilled in the art, given the guidance provided in the instant specification, can readily determine whether a given function of a birtoxin or parakinin family polypeptide is preserved. One such function is binding to an ion channel or elicitation of a kinin response by a protein of the invention. The term "scorpion toxin family polypeptide" also includes isoforms of birtoxin or parakinin family polypeptides.

Furthermore, those skilled in the art will also appreciate that changes can be made to scorpion toxin family polypeptides which alter the function of the scorpion toxin family polypeptide, i.e. alter the binding affinity of the peptide for its target or alter the target specificity of the protein. Typically such function-altering changes are made at residues that affect the binding site of the polypeptide or the folding of the polypeptide. One such change is exemplified herein by the differing biological activities of birtoxin and ikitoxin, which differ in amino acid sequence at only the 23rd residue, which is a glycine in birtoxin and a glutamic acid residue in ikitoxin. Another such change is exemplified herein by the differing biological activities of dortoxin and bestoxin, which have a two amino acid difference of Lys20 in dortoxin to Glu20 in bestoxin and Glu45 in dortoxin to Ser45 in bestoxin.

Whether a birtoxin family polypeptide binds to an ion channel (or fragment thereof) is readily determined, using any known assay for protein-protein binding, including that described in Little et al. (J. Biol. Chem. (1998) 273:27076–28083) and others described herein. Methods for measuring kinin activity are well known in the art (Marceau et al., Peptides. 2001 22:1397–402; Giragossian et al Immunopharmacology. 1999 43:169–77; Meini et al J Pharmacol Exp Ther. 1999 289:1250–6).

The term "scorpion toxin family polypeptide" encompasses a polypeptide comprising 6 or more contiguous amino acids of an of the sequences depicted in SEQ ID NOS:1–5 and 27–30. Thus, the term "scorpion toxin family polypeptide" encompasses a polypeptide comprising at least about 5, 10, 15, 20, 25, 30, 35, 40, 45, 50, or 55 amino acids of any of the sequences set forth in SEQ ID NOS:1–5 and 27–30. In some embodiments, a scorpion family polypeptide has the entire sequence as shown in SEQ ID NOS:1–5 and 27–30.

Also encompassed by the term "scorpion toxin family polypeptide" is a polypeptide sharing at least about. 60%, preferably at least about 70%, more preferably at least about 80%, even more preferably at least about 85%, even more preferably at least about 87%, 90%, 95%, 98%, or 99% or more amino acid sequence identity with the sequence depicted in SEQ ID NOS:1–5 and 27–30.

Also included in the term "scorpion toxin family polypeptide" are antigenic epitopes of a scorpion toxin family polypeptide. Those skilled in the art can readily determine which peptide fragments are antigenic epitopes. As a non-limiting example of how one can determine which region(s) of a protein are likely to be exposed on the surface (i.e., hydrophilic domains), and therefore potentially antigenic, one can analyze the amino acid sequence using Kyte-Doolittle hydropathicity analysis and/or Hopp-Woods hydrophilicity analysis. Kyte and Doolittle (1982) J. Mol. Biol. 157:105; and Hopp and Woods (1981) Proc. Natl. Acad. Sci. USA 78:3824.

Production of Scorpion Venom Polypeptides

Because the amounts of scorpion toxin family polypeptides that can be obtained by purifying scorpion venom as described herein are small, the polypeptides useful in the invention may also be produced by other techniques, such as recombinant techniques or solid phase synthesis. By constructing a nucleic acid encoding a birtoxin or parakinin family polypeptide, e.g. a nucleic acid encoding any of the polypeptides of SEQ ID NOS: 1–5 and 27–30, or fragments thereof, one may obtain large amounts of scorpion toxin family polypeptides.

The scorpion venom polypeptide encoding nucleic acid may be constructed by a variety of conventional methods including, but not limited to, cloning of the gene from scorpion DNA or RNA extracts and standard recombinant DNA techniques (See Maniatis, Cold Spring Harbor). An alternative is to synthesize overlapping oligonucleotides, followed by annealing and extension of these oligonucleotides to produce a double-stranded DNA molecule encoding the peptide sequence of a birtoxin family polypeptide, together with flanking sequence necessary to accomplish insertion of the synthetic scorpion venom polypeptide-encoding nucleic acid into a suitable expression plasmid. These oligonucleotides may be synthesized using a commercial DNA synthesizer such as the ABI model 391 DNA Synthesizer (Applied Biosystems).

Codon usage may be optimized for high-level expression in an expression system. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the protein will benefit from native folding and post-translational modifications. Small peptides can also be synthesized in the laboratory. Polypeptides that are subsets of the complete amino acid sequence may be used to identify and investigate parts of the protein important for function, or to raise antibodies directed against these regions.

When expressing these subject polypeptides, it may be desirable express a subject polypeptide operably linked to a secretion signal sequence to facilitate secretion of the polypeptide from the cell. In other embodiments, the subject polypeptide may be operably linked to second polypeptide, e.g. GST, His-tag, MBP, etc in order to facilitate the purification of the subject polypeptide.

Alternatively, one may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential additional of activated monomeric units, for example amino acids and modified amino acids, in particular modified amino acids to a solid phase bound growing peptide chain.

The small size of the bradykinin-like family polypeptides of the invention in combination with a potential modified N-terminal proline residue makes them particularly suitable for synthesis using solid phase peptide synthesis methods.

Recombinant Vectors of the Invention

The present invention further provides recombinant vectors ("constructs") comprising scorpion toxin family polynucleotides of the invention. Recombinant vectors are useful for propagation of the subject scorpion toxin family polynucleotides (cloning vectors). They are also useful for effecting expression of a scorpion toxin family polynucleotide in a cell (expression vectors). Some vectors accomplish both cloning and expression functions. The choice of appropriate vector is well within the skill of the art. Many such vectors are available commercially.

A variety of host-vector systems may be utilized to propagate and/or express the scorpion toxin family polynucleotides of the invention. Such host-vector systems represent vehicles by which coding sequences of interest may be produced and subsequently purified, and also represent cells that may, when transformed or transfected with the appropriate nucleotide coding sequences, produce scorpion toxin family polypeptides of the invention. These include, but are not limited to, microorganisms (e.g., *E. coli*, *B. subtilis*) transformed with recombinant bacteriophage vectors, plasmid DNA, or cosmid DNA vectors comprising scorpion toxin family polynucleotides; yeast (e.g., Saccharomyces, Pichia) transformed with recombinant yeast vectors comprising scorpion toxin family polynucleotides); insect cell systems (e.g., Spodoptera frugiperda) infected with recombinant virus expression vectors (e.g., baculovirus vectors, many of which are commercially available, including, for example, pBacPAK8, and BacPAK6) comprising scorpion toxin family polynucleotides; plant cell systems; or mammalian cell systems (e.g., COS, CHO, BHK, 293, 3T3) harboring recombinant vectors comprising mammalian promoters (e.g., metallothionein promoter) or promoters from viruses which replicate in mammalian cells (e.g., adenovirus late promoter; vaccinia virus promoter, and the like). Examples of prokaryotic cloning vectors which find use in propagating scorpion toxin family polynucleotides of the invention are pBR322, M13 vectors, pUC18, pcDNA, and pUC19. Prokaryotic expression vectors which find use in expressing scorpion toxin family polypeptides in prokaryotic cells include pTrc99A, pK223-3, pEZZ18, pRIT2T, and pMC1871. Eukaryotic expression vectors which find use in expressing scorpion toxin family polynucleotides and scorpion toxin family polypeptides in eukaryotic cells include commercially available vectors such as pSVK3, pSVL, pMSG, pCH110, pMAMneo, pMAMneo-LUC, pPUR, and the like.

Generally, a bacterial host will be transformed to contain the expression system using a vector. A variety of vectors may be employed so long as they introduce the expression system into the host in a manner whereby the product encoded by the expression system can be expressed. Thus, the vector could be one that is capable homologously recombining with a region of the host chromosome such that the expression system becomes integrated into the host chromosome such that expression of the protein encoded thereby can occur. See Thomas and Capecchi (1987) Cell 51:503–512; as well as U.S. Pat. Nos. 5,631,153; 5,627,059; 5,487,992 and 5,464,764, the disclosure of which is herein incorporated by reference.

Generally, the expression cassette will be a plasmid that provides for expression of the encoded scorpion toxin family polypeptide under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and ColE1. Expression vectors generally have convenient restriction sites located near the promoter sequence to provide for the insertion of nucleic acid sequences encoding heterologous proteins. In addition, the expression vector will also typically comprise a marker which provides for detection of the clones that have been transformed with the vector. A variety of markers are known and may be present on the vector, where such markers include those that confer antibiotic resistance, e.g. resistance to ampicillin, tetracycline, chloramphenicol, kanamycin (neomycin), markers that provide for histochemical detection, etc. Specific vectors that may find use in the subject methods include: pBR322, pUC18, pUC19, pcDNA, and the like. Introduction of the nucleic acid encoding the subject peptidic product into the expression vector is accomplished by cutting the expression vector and inserting the polynucleotide encoding the desired product.

Following preparation of the expression vector comprising the nucleic acid, the expression vector will be introduced into an appropriate host cell for production of the scorpion toxin family polypeptide, i.e. a host cell will be transformed with the expression vector. Transformation of host cells may be accomplished in any convenient manner, where two representative means of transformation are treatment with divalent cation transformation compositions and electrotransformation. In transformation through divalent cation treatment, the host cells are typically incubated with the one or more divalent cations, e.g. CaCl2, which serves to make the host cell permeable to the vector DNA. See Cohen et al. (1972) Proc. Nat'l. Acad. Sci. USA 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al. (1988) Nucleic Acids Research 16:6127.

A variety of host cells are suitable and may be used in the production of the scorpion toxin family polypeptides, where such host cells may be bacterial cells, yeast cells, or other cells, such as plant cells (see Depicker (1982) J. Mol. Appl. Gen. 1:561, where the host cell will generally be bacterial, e.g. *E. coli*, *B. subtilis*, where an *E.coli* strain is often the host cell of choice; or mammalian, e.g., COS, CHO, 3T3, and the like. *E. coli* strains that may be used include DH1, DH5, MM294, LE392, MC1061 and JM109.

Following transformation, bacterial host cells are screened for incorporation of the expression vector. Transformed colonies, e.g. host cells harboring the expression vector with the nucleic acid encoding the scorpion toxin family polypeptide are identified, and then grown up in large quantity. Where appropriate, agents that induce expression of the scorpion toxin family polypeptide are contacted with the host cell.

Following colony growth, the expressed product will be harvested and purified for subsequent use. Typically, purification of the product involves disruption of the host cell, inactivation and removal of the native host proteins and precipitation of the nucleic acids. The product is separated from the other host cell constituents using one or more of a number of separation techniques known to those of skill in the art, e.g. centrifugation, dialysis, gel filtration chromatography, ion exchange chromatography, and the like. See Guide to Protein Purification (Murray P. Deutscher ed., Harcourt Brace & Co.)(1990). Using these protein purification techniques, isolated product may be prepared, where by isolated is meant a composition that is at least about 95% by weight peptidic product, usually at least about 98% by weight peptidic product and more usually at least about 99% by weight product, when the composition is dehydrated, e.g. lyophilized.

The subject nucleic acid molecules are generally propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence.

Other vectors are suitable for expression in cells in culture. These vectors will generally include regulatory sequences ("control sequences" or "control regions") which are necessary to effect the expression of a scorpion toxin family polynucleotide to which they are operably linked. Still other vectors are suitable for transfer and expression in cells in a whole organism or person.

The scorpion toxin family polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly, Cancer Gene Therapy (1994) 1:51–64; Kimura, Human Gene Therapy (1994) 5:845–852; Connelly, Human Gene Therapy (1995) 1:185–193; and Kaplitt, Nature Genetics (1994) 6:148–153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5, 219,740; WO 93/11230; WO 93/10218; Vile and Hart, Cancer Res. (1993) 53:3860–3864; Vile and Hart, Cancer Res. (1993) 53:962–967; Ram et al., Cancer Res. (1993) 53:83–88; Takamiya et al., J. Neurosci. Res. (1992) 33:493–503; Baba et al., J. Neurosurg. (1993) 79:729–735; U.S. Pat. No. 4,777,127; GB Patent No. 2,200,651; and EP 345 242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822–3828; Mendelson et al., Virol. (1988) 166:154–165; and Flotte et al., PNAS (1993) 90:10613–10617.

Also of interest are adenoviral vectors, e.g., those described by Berkner, Biotechniques (1988) 6:616–627; Rosenfeld et al.(1991) Science 252:431–434; WO 93/19191; Kolls et al. (1994) Proc. Natl. Acad. Sci. USA 91:215–219; Kass-Eisler et al. (1993) Proc. Natl. Acad. Sci. USA 90:11498–11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) Hum. Gene Ther. 3:147–154; ligand linked DNA, for example see Wu (1989) J. Biol. Chem. 264:16985–16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell Biol. 14:2411–2418, and in Woffendin (1994) Proc. Natl. Acad. Sci. 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT Nos. WO 95/13796, WO 94/23697, and WO 91/14445, and EP No. 524 968.

Further non-viral delivery suitable for use includes mechanical delivery systems such as the approach described in Woffendin et al.(1994) Proc. Natl. Acad. Sci. USA 91:11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Host Cells of the Invention

The present invention further provides host cells, which may be isolated host cells, comprising scorpion toxin family polynucleotides of the invention. Suitable host cells include prokaryotes such as *E. coli, B. subtilis*, eukaryotes, including insect cells in combination with baculovirus vectors, yeast cells, such as Saccharomyces cerevisiae, or cells of a higher organism such as vertebrates, including amphibians (e.g., Xenopus laevis oocytes), and mammals, particularly mammals, e.g. COS cells, CHO cells, 293 cells, 3T3 cells, and the like, may be used as the expression host cells. Host cells can be used for the purposes of propagating a scorpion toxin family polynucleotide, for production of a scorpion toxin family polypeptide, or in cell-based methods for identifying agents which modulate a level of scorpion toxin family mRNA and/or protein and/or enzyme activity in a cell.

The subject nucleic acids can be used to generate site specific gene modifications in cell lines. The modified cells are useful in the study of scorpion toxin family function and regulation. For example, a series of small deletions or substitutions may be made in the scorpion toxin family polynucleotide to determine the role of different coding regions in ion channel binding, kinin receptor binding, etc.

DNA constructs for homologous recombination will comprise at least a portion of the scorpion toxin family gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527–537.

Antibodies Specific for Scorpion Venom

Toxin Family Polypeptides

The present invention provides antibodies, which may be isolated antibodies, specific for scorpion toxin family polypeptides of the invention. Such antibodies are useful, for example, in methods of detecting the presence of scorpion toxin family polypeptide in a biological sample, in methods of isolating a scorpion toxin family polypeptide from a biological sample, and in methods of producing antivenom preparations The scorpion toxin family polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a scorpion toxin family polypeptide.

In some embodiments, an antibody of the invention modulates scorpion toxin family polypeptide-ion channel binding. An antibody of the invention which modulates scorpion toxin family polypeptide-ion channel binding is one that specifically modulates binding of a scorpion toxin family polypeptide to an ion channel polypeptide, when compared to a suitable control. An antibody which "specifically modulates" scorpion toxin family polypeptide-ion channel binding is one that does not substantially inhibit interaction of other protein-protein binding at the concentration required to achieve 50% change in scorpion toxin family polypeptide-ion channel binding. Antibody modulation of scorpion toxin family polypeptide-ion channel binding can be measured by any suitable assay, including, but not limited to an enzyme-linked immunosorbent assay (ELISA), a radioimmunoassay (RIA), and the like. Ion channel activity may be measured by methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.)

Typically, these assays are carried out in the presence of various concentrations of antibody. A suitable control is a sample that contains the scorpion toxin family polypeptide and ion channel proteins, and no antibody, or, alternatively, the sample contains scorpion toxin family polypeptide and ion channel proteins and a non-specific antibody, e.g., an antibody specific for albumin, or an anti-idiotype antibody.

Antibodies may be raised to the wild-type or variant forms. Antibodies may be raised to isolated peptides corresponding to ion channel-binding domain(s) of native scorpion toxin family polypeptide, to isolated peptide corresponding to solvent-accessible portions of native scorpion toxin family polypeptide, or to isolated peptides corresponding to a non-ion channel-binding domain of scorpion toxin family polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

Compositions of the Invention

The present invention further provides compositions comprising the polypeptides, polynucleotides, recombinant vectors, host cells, scorpion toxin family polypeptide-ion channel binding modulators, agents, pharmacophores, and antibodies of the invention. These compositions may include a buffer, which is selected according to the desired use of the polypeptide, polynucleotide, recombinant vector, host cell, scorpion toxin family polypeptide-ion channel binding inhibitor, kinin analog, kinin antagonist, or antibody, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995) Mack Publishing Co.

Pharmacophores

A pharmacophore is a compound that has a specific biochemical activity which is obtained by the 3-dimensional physical shape of the compound and the electrochemical properties of the atoms making up the compound. Specific pharmacophores of the invention are defined by the structural aspects of the conserved binding surfaces a birtoxin family or parakinin family polypeptide. Thus a pharmacophore of the invention can have a shape (i.e., the geometric specifications) substantially as defined by its amino acid sequence and folding (see, for example, the proposed model structures of birtoxin and ikitoxin in FIGS. 4B, 8A, or 8B), and more specifically as defined by the interface regions between a birtoxin family polypeptide and an ion channel protein or a parakinin family polypeptide and a kinin receptor. The term "pharmacophore" is meant to encompass synthetic, naturally occurring, or recombinantly produced molecules (e.g., small molecule; drugs; peptides; antibodies (including antigen-binding antibody fragments, e.g., to provide for passive immunity); endogenous factors present in eukaryotic or prokaryotic cells (e.g., polypeptides, plant extracts, and the like); etc.). Of particular interest are screening assays for agents that have a low toxicity for human cells.

Pharmacophores encompass numerous chemical classes, including organic molecules, such as small organic compounds having a molecular weight of more than 50 and less than about 2,500 daltons. Pharmacophores comprise functional groups necessary for structural interaction with proteins, particularly hydrogen bonding, and typically include at least an amine, carbonyl, hydroxyl or carboxyl group, preferably at least two of the functional chemical groups. The pharmacophores often comprise cyclical carbon or heterocyclic structures and/or aromatic or polyaromatic structures substituted with one or more of the above functional groups. Pharmacophores are also found among biomolecules including, but not limited to: peptides, saccharides, fatty acids, steroids, purine and/or pyrimidine containing structures, derivatives, structural analogs or combinations thereof.

Pharmacophores can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The pharmacophores of the present invention can be identified using the 3D structural aspects of the binding surfaces of RNA polymerases. One exemplary method for identifying structures that selectively bind to one or more ion channels are described as follows.

Rational Design of Pharmacophores

The shape that the scorpion venom toxin family polypeptides adopts at its binding surfaces when bound to e.g. an ion channel or kinin receptor, the biological shape, is an essential component of its biological activity. This shape, and any specific interactions such as hydrogen bonds, can be exploited to derive predictive models used in rational drug design. These can be used to optimize lead compounds, design de novo compounds, and search databases of existing compounds for novel structures possessing the desired biological activity. In order to aid in the discovery of useful pharmacophores for the interface binding surface, these models must make useful predictions, relate chemical structures to activity, and be confidently extrapolated to chemical classes beyond those used for model derivation.

Pharmacophore models (e.g., BioCAD incorporated herein by reference) model activity in terms of the positions of a small number of atoms of particular functional groups. This overcomes many of the problems of traditional QSAR models. U.S. Pat. No. 5,025,388 to Kramer et al. provides for comparative molecular field analysis (COMFA incorporated herein by reference) methodology. In accordance with this methodology the 3-dimensional structure for each molecule is placed within a 3-dimensional lattice and a probe atom is chosen, placed successively at each lattice intersection and the steric and electrostatic interaction energies between the probe atom and the molecule are calculated for all lattice intersections. The energies are listed in a 3-dimensional-QSAR table. A field fit procedure is applied by choosing the molecule with the greatest biological activity as the reference in conforming the remaining molecules to it.

U.S. Pat. No. 5,436,850 (incorporated herein by reference in its entirety) describes a computer-assisted method for identifying protein sequences that interact with known protein structures. The method uses a known three-dimensional protein structure and determines three key features of each residue's environment within the structure: (1) the total area of the residue's side-chain that is buried by other protein atoms, inaccessible to solvent; (2) the fraction of the side-chain area that is covered by polar atoms (O, N) or water, and (3) the local secondary structure. Based on these parameters, each residue position is categorized into an environment class. In this manner, a three-dimensional protein structure is converted into a one-dimensional environment string, which represents the environment class of each residue in the folded protein structure. A 3D structure profile table is then created containing score values that represent the frequency of finding any of the 20 common amino acids structures at each position of the environment string. These frequencies are determined from a database of known protein structures and aligned sequences. The method determines the most favorable alignment of a target protein sequence to the residue positions defined by the environment string, and determines a "best fit" alignment score for the target sequence.

The methodology disclosed within U.S. Pat. No. 5,526,281 (incorporated herein by reference in its entirety) is also useful for the generation of pharmacophores of birtoxin family polypeptides. The approach disclosed within the '281 patent thus allows the user to focus on the salient features of the molecule. The first step in the '281 method for generating pharmacophores involves the selection of a pose. A pose of a molecule is defined by its confirmation (internal torsional angles of the rotatable bonds) and orientation (the rigid rotations and translations). The negative image of the pose can also be generated and as such represents a pose for the corresponding binding surface of homologous and/or heterologous interactions with other viral polymerases. The negative image and other possible pharmacophores can be generated using software available such as Catalyst™ from BioCad, Foster City, Calif. and, Batchmin™ available from Columbia University, New York City, N.Y. (both of which are incorporated herein by reference). These programs take into consideration various properties including physical and chemical properties, Shape, electrostatic interaction, solvation and biophysical properties.

Other methods for generating pharmacophores of the present invention are disclosed within U.S. Pat. Nos. 5,884,230, 5,307,287, and 5,434,796, each of which are incorporated herein by reference in their entirety.

In general, then, the invention contemplates computer comprising a representation of a pharmacophore of the invention in computer memory. In this embodiment, the pharmacophore is represented as a three-dimensional array of points defining a specific shape and volume. The three-dimensional array of points is generally an aggregate average shape of a molecule (or a plurality of molecules) when that molecule optimally interacts with the interface regions of e.g. an ion channel in a manner that results modulation of ion channel activity, birtoxin family polypeptide activity or birtoxin family polypeptide-ion channel interaction. This three-dimensional array of points can be represented by a coordinate system configured in computer memory. The computer or computer system can thus be used to design a molecular structure that can modulate ion channel activity, e.g. birtoxin family polypeptide activity or birtoxin family polypeptide-ion channel interaction as described herein, and can further be used to screen candidate molecular structures for the ability to modulate e.g. ion channel activity, birtoxin family polypeptide activity or birtoxin family polypeptide-ion channel interaction.

Methods of Using the Polypeptides and Polynucleotides of the Invention

The present invention provides a variety of detection methods, which methods are useful in diagnostic assays. Also provided are a variety of screening assays, which assays are useful for identifying agents which affect scorpion venom polypeptide activity (e.g., ion channel or kinin receptor binding) and/or scorpion venom polypeptide mRNA and/or polypeptide levels.

Detection Methods

Detection methods of the present invention include methods for detecting scorpion venom polypeptides in a biological sample, methods for detecting scorpion venom family mRNA in a biological sample, and methods for detecting scorpion venom polypeptide-ion channel binding scorpion venom polypeptide-kinin receptor and activity in a biological sample.

The detection methods can be provided as part of a kit. Thus, the invention further provides kits for detecting the presence and/or a level of scorpion venom polypeptide or scorpion venom-encoding polynucleotides in a biological sample. Procedures using these kits can be performed by clinical laboratories, experimental laboratories, medical practitioners, or private individuals. The kits of the invention for detecting a scorpion venom polypeptide comprise a moiety that specifically binds scorpion venom polypeptide, including, but not limited to, a scorpion venom polypeptide-specific antibody, and an ion channel polypeptide or kinin receptor. The kits of the invention for detecting a scorpion venom polypeptide-encoding polynucleotide comprise a moiety that specifically hybridizes to a scorpion venom polypeptide-encoding polynucleotide. The kit may optionally provide additional components that are useful in the procedure, including, but not limited to, buffers, developing reagents, labels, reacting surfaces, means for detections, control samples, standards, instructions, and interpretive information.

Methods of Detecting Scorpion Toxin Family Polypeptide in a Biological Sample

The present invention further provides methods for detecting the presence and/or measuring a level of a scorpion toxin family polypeptide in a biological sample, using a scorpion toxin family polypeptide-specific antibody. The methods generally comprise:

a) contacting the sample with an antibody specific for a scorpion venom toxin family polypeptide; and b) detecting binding between the antibody and molecules of the sample.

Detection of specific binding of the scorpion venom toxin family polypeptide-specific antibody, when compared to a suitable control, is an indication that scorpion venom toxin family polypeptides are present in the sample. Suitable controls include a sample known not to contain a scorpion venom toxin polypeptide; and a sample contacted with an antibody not specific for a scorpion venom toxin polypeptide, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the scorpion venom toxin polypeptide-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., 152 Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for scorpion venom toxin polypeptide-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled scorpion venom toxin polypeptide-specific antibody. Detection methods are known in the art and will be chosen as appropriate to the signal emitted by the detectable label. Detection is generally accomplished in comparison to suitable controls, and to appropriate standards.

The present invention further provides methods for detecting the presence and/or measuring a level of birtoxin family polypeptide in a biological sample. The methods generally comprise:

a) contacting the sample with a ion channel protein specific for a birtoxin family polypeptide; and b) detecting binding between the ion channel protein and molecules of the sample.

Detection of specific binding of the ion channel polypeptide is an indication that birtoxin family polypeptides are present in the sample.

The present invention further provides methods for detecting the presence and/or measuring a level of parakinin family polypeptide in a biological sample. The methods generally comprise:

a) contacting the sample with a kinin receptor, e.g. the parakinin receptor, specific for a parakinin family polypeptide; and b) detecting binding between the kinin receptor and molecules of the sample.

Detection of specific binding of the receptor polypeptide is an indication that parakinin family polypeptides are present in the sample.

Methods for detecting binding between a scorpion toxin polypeptide and an ion channel or kinin receptor polypeptide are known in the art and include immunoprecipitation of scorpion toxin complexes using an antibody specific to the scorpion venom toxin or ion channel/kinin receptor, as long as the antibody does not disrupt birtoxin family polypeptide-ion channel/receptor binding. Alternatively, the ion channel polypeptide used may be a fusion protein which provides for specific immunoprecipitation of the fusion partner, an enzymatic detection, a fluorescent signal (e.g., a green fluorescent protein). The ion channel/receptor polypeptide can be labeled with any detectable label, as described below. The ion channel polypeptide can be attached, directly or through a linker, to an insoluble support (e.g., polystyrene beads, magnetic beads, and the like), thereby providing a means for separating scorpion toxin family polypeptide-ion channel/receptor complexes from the biological sample, and subsequently detecting the presence of and/or measuring the amount (level) of scorpion venom toxin polypeptide.

Binding of birtoxin family polypeptide to the ion channel may also be detected by monitoring ion channel activity, using methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.)

Methods of Detecting Scorpion Venom Toxin Family Polypeptide MRNA in a Biological Sample The present invention further provides methods for detecting the presence of scorpion venom polypeptide mRNA in a biological sample. The methods can be used, for example, to assess whether a test compound affects scorpion venom polypeptide gene expression, directly or indirectly.

The methods generally comprise:

a) contacting the sample with a scorpion venom polypeptide-encoding polynucleotide of the invention under conditions which allow hybridization; and b) detecting hybridization, if any.

Detection of hybridization, when compared to a suitable control, is an indication of the presence in the sample of a scorpion venom polypeptide-encoding polynucleotide. Appropriate controls include, for example, a sample which is known not to contain scorpion venom polypeptide-encoding polypeptide mRNA, and use of a labeled polynucleotide of the same "sense" as a scorpion venom polypeptide mRNA. Conditions which allow hybridization are known in the art, and have been described in more detail above. Detection can be accomplished by any known method, including, but not limited to, in situ hybridization, PCR, RT-PCR, and "Northern" or RNA blotting, or combinations of such techniques, using a suitably labeled scorpion venom polypeptide polynucleotide. A variety of labels and labeling methods for polynucleotides are known in the art and can be used in the assay methods of the invention. Specific hybridization can be determined by comparison to appropriate controls.

Methods using PCR amplification can be performed on the DNA from a single cell, although it is convenient to use at least about 105 cells. The use of the polymerase chain reaction is described in Saiki et al. (1985) Science 239:487, and a review of current techniques may be found in Sambrook, et al. Molecular Cloning: A Laboratory Manual, CSH Press 1989, pp. 14.2B14.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4=,5=-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N=,N=-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Methods for Detecting Birtoxin Family Polypeptide-Ion Channel Activity in a Biological Sample The present invention provides a method for detecting a birtoxin family polypeptide-ion channel binding activity in a biological sample. The method generally comprises:

a) contacting a sample containing ion channel with a birtoxin family polypeptide; and b) detecting binding of birtoxin family polypeptide to ion channel.

Methods for detecting binding between a birtoxin family polypeptide and an ion channel polypeptide are known in the art and include immunoprecipitation of birtoxin family polypeptide-ion channel complexes using an antibody specific to birtoxin family polypeptide or ion channel, as long as the antibody does not disrupt birtoxin family polypeptide-ion channel binding. Alternatively, the ion channel polypeptide used may be a fusion protein which provides for specific immunoprecipitation of the fusion partner, an enzymatic detection, a fluorescent signal (e.g., a green fluorescent protein). The ion channel polypeptide can be labeled with any detectable label, as described below. The ion channel polypeptide can be attached, directly or through a linker, to an insoluble support (e.g., polystyrene beads, magnetic beads, and the like), thereby providing a means for separating birtoxin family polypeptide-ion channel complexes from the biological sample, and subsequently detecting the presence of and/or measuring the amount (level) of birtoxin family polypeptide.

Binding of birtoxin family polypeptide to the ion channel may also be detected by monitoring ion channel activity, using methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.)

The method can also be used to measure a level of birtoxin family polypeptide-ion channel binding activity in a biological sample. In these methods, a series of positive controls is provided, with birtoxin family polypeptide at various, known concentrations, and a fixed amount of ion channel protein, thereby generating a standard curve. In this manner, a level of birtoxin family polypeptide-ion channel binding can be compared to the standard curve, and the amount of birtoxin family, polypeptide-ion channel binding activity determined.

The method is useful, for example, in assessing the specificity of a birtoxin family polypeptide for a particular type or subtype of ion channel.

Screening Assays

The present invention provides screening methods for identifying agents which modulate birtoxin family polypeptide-ion channel binding activity, methods for identifying agents which birtoxin family polypeptide-ion channel interaction, methods for identifying agents which modulate a level of birtoxin family polypeptide in a cell, and methods for identifying agents which modulate a level of birtoxin family polypeptide mRNA in a cell. The present invention also provides screening methods for identifying agents which modulate kinin polypeptide-kinin receptor binding activity, methods for identifying agents which modulate kinin family polypeptide-ion channel interaction, methods for identifying agents which modulate a level of parakinin family polypeptide in a cell, and methods for identifying agents which modulate a level of kinin family polypeptide mRNA in a cell.

As used herein, the term "modulate" encompasses "increase" and "decrease". Of particular interest are agents which modulate birtoxin family polypeptide-ion channel binding activity, and/or which modulate birtoxin family polypeptide-ion channel interaction, and/or which modulate a level of birtoxin family polypeptide in a cell, and/or which modulate a level of birtoxin family polypeptide mRNA in a cell. Such agents are of interest as candidates for treating diseases or disorders associated with ion channels, including, but not limited to those associated with chloride channels (e.g., epilepsy, renal tubular disorders, Bartter's syndrome, cystic fibrosis, steopetrosis, Angleman or Prader-Willi, upregulation of choride channels in glioma cells, etc.), sodium channels (e.g.,Hyperkalemic periodic paralysis, hypokalemic periodic paralysis, congenital Paramyotonia, Myotonia Fluctuans, Myotonia Permanens, Acetzolamide-responsive myotonia, malignant hyperthermia, nerve injury, epilepsy, various heart diseases, thyroid, endocrine, etc.), calcium channels (e.g., self-biting & self-injurious behavior, hypokalemic periodic paralysis, malignant hyperthermia, Lambert-Eaton Myasthenic Syndrome, Episodic ataxia type-2, familial hemiplegic migraine, progressive ataxia, central core disease, granulomatous myopathy, ventricular tachycardia, cardiomyopathy, etc.), and potassium channels (e.g., neuromyotonia, hypokalemic periodic paralysis, Andersen syndrome, Bartter syndrome, long-QT syndromes, Jervell & Lange-Nielsen Syndrome, episodic ataxia, myokymia ayndrome, hyperinsulinemic hypoglycemia of infancy, non-syndromic hearing loss, etc.). Such agents are also of interest in creating novel insecticides or rodenticides where the agent primarily modulates ion channels in insects or rodents. Also of particular interest are agents which modulate kinin-kinin receptor binding activity. Such agents are of interest as candidates for treating disease and conditions associated with kinins, including, but not limited to pain management, inflammation, hyperanalgesia, pathological conditions of the cardiovascular system, septic shock, anaphylaxis, rhinitis, asthma, inflammatory bowel disease acute pancreatitis, post-gastrectomy dumping syndrome, carcinoid syndrome, migraine and angioneurotic edema. Furthermore, such agents may also be used in medical procedures, to, for example, modulate the permeability of the blood brain barrier, or vasodilation.

The terms "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Furthermore, pharmacophores may be designed based on the structural aspects of the ion channel/receptor binding interfaces of scorpion venom toxin polypeptides.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C.

and 40° C. Incubation periods are selected for optimum activity, but may also be optimized to facilitate rapid high-throughput screening. Typically between 0.1 and 1 hour will be sufficient.

Methods for Identifying Agents that Modulate Birtoxin Family Polypeptide-Ion Channel Binding Activity The present invention provides methods of identifying agents which modulate ion channel binding activity of a birtoxin family polypeptide of the invention. The term "modulate" encompasses an increase or a decrease in the measured birtoxin family polypeptide-ion channel binding activity when compared to a suitable control.

The method generally comprises:

a) contacting a substance to be tested with a sample containing a birtoxin family polypeptide and an ion channel; and b) measuring ion channel binding activity of the birtoxin family polypeptide in the presence of the substance.

An increase or a decrease in ion channel binding activity in comparison to ion channel binding activity in a suitable control (e.g., a sample comprising a birtoxin family polypeptide and an ion channel in the absence of the substance being tested) is an indication that the substance modulates a ion channel binding activity of the birtoxin family polypeptide.

Methods for practicing such assays are known to those of skill in the art. (See, e.g., Mishina et al. (1985) Nature 313:364–369; and Noda, et al. Nature 322:836–828.) Ion channel activity may be measured by methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.)

An "agent which modulates birtoxin family polypeptide-ion channel binding activity", as used herein, describes any molecule, e.g. synthetic or natural organic or inorganic compound, protein or pharmaceutical, with the capability of altering ion channel binding activity of a birtoxin family polypeptide, as described herein. Generally a plurality of assay mixtures are run in parallel with different agent concentrations to obtain a differential response to the various concentrations. Typically, one of these concentrations serves as a negative control, i.e. at zero concentration or below the level of detection. Ion channel binding can be measured as described hereinabove.

An agent which modulates ion channel binding activity of a birtoxin family polypeptide increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents which increase or decrease ion channel binding activity of a birtoxin family polypeptide to the desired extent may be selected for further study, and assessed for cellular availability, cytotoxicity, biocompatibility, etc.

Methods for Identifying Agents that Modulate Parakinin family Polypeptide-Ion Channel Binding Activity The present invention provides methods of identifying agents which modulate kinin, e.g. bradykinin binding activity of a parakinin family polypeptide of the invention. The term "modulate" encompasses an increase or a decrease in the measured parakinin family polypeptide-receptor binding activity when compared to a suitable control.

The method generally comprises:

a) contacting a substance to be tested with a sample containing a parakinin family polypeptide and a receptor e.g. a bradykinin receptor; and b) measuring receptor binding activity of the parakinin family polypeptide in the presence of the substance.

An increase or a decrease in receptor binding activity in comparison to receptor binding activity in a suitable control (e.g., a sample comprising a parakinin family polypeptide and an receptor in the absence of the substance being tested) is an indication that the substance modulates a receptor binding activity of the parakinin family polypeptide.

An "agent which modulates parakinin family polypeptide-receptor binding activity", as used herein, describes any molecule, e.g. synthetic or natural organic or inorganic compound, protein or pharmaceutical, with the capability of altering receptor binding activity of a birtoxin family polypeptide, as described herein. Generally a plurality of assay mixtures are run in parallel with different agent concentrations to obtain a differential response to the various concentrations. Typically, one of these concentrations serves as a negative control, i.e. at zero concentration or below the level of detection. Receptor binding can be measured as described hereinabove.

An agent which modulates receptor binding activity of a parakinin family polypeptide increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents which increase or decrease receptor binding activity of a parakinin family polypeptide to the desired extent may be selected for further study, and assessed for cellular availability, cytotoxicity, biocompatibility, etc.

Further assays, such as in vivo assays, where a parakinin family polypeptide are administered to a subject and the amount of pain measured, are also envisioned.

Methods of Detecting Agents which Modulate a Level of Scorpion Venom Toxin Polypeptide MRNA and/or Polypeptide A wide variety of cell-based assays may be used for identifying agents which modulate levels of scorpion venom toxin polypeptide mRNA, using, for example, a mammalian cell transformed with a construct comprising a scorpion venom toxin polypeptide-encoding cDNA such that the cDNA is overexpressed, or, alternatively, a construct comprising a scorpion venom toxin gene promoter operably linked to a reporter gene.

Accordingly, the present invention provides a method for identifying an agent, particularly a biologically active agent, that modulates a level of scorpion venom toxin polypeptide expression in a cell, the method comprising: combining a candidate agent to be tested with a cell comprising a nucleic acid which encodes a scorpion venom toxin polypeptide; and determining the effect of said agent on scorpion venom toxin polypeptide expression. A modulation of scorpion venom toxin polypeptide expression levels includes increasing the level and decreasing the level of scorpion venom toxin polypeptide mRNA and/or scorpion venom toxin encoded by the scorpion venom toxin polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of birtoxin family polypeptide mRNA and/or polypeptide following contacting the cell with a candidate agent being tested, compared to a control to which no agent is added, is an indication that the agent modulates scorpion venom toxin polypeptide expression.

An agent being tested for its effect on scorpion venom toxin polypeptide expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures or may be immortalized cell lines.

Scorpion venom toxin family polypeptide mRNA and/or polypeptide whose levels are being measured can be encoded by an endogenous scorpion venom toxin polynucleotide, or the scorpion venom toxin polynucleotide can be one that is comprised within a recombinant vector and introduced into the cell, i.e., the scorpion venom toxin polypeptide mRNA and/or polypeptide can be encoded by an exogenous scorpion venom toxin polynucleotide. For example, a recombinant vector may comprise an isolated scorpion venom toxin polypeptide transcriptional regulatory sequence, such as a promoter sequence, operably linked to a reporter gene (e.g,. β-galactosidase, CAT, luciferase, or other gene that can be easily assayed for expression). In these embodiments, the method for identifying an agent that modulates a level of scorpion venom toxin polypeptide expression in a cell, comprises: combining a candidate agent to be tested with a cell comprising a nucleic acid which comprises a scorpion venom toxin gene transcriptional regulatory element operably linked to a reporter gene; and determining the effect of said agent on reporter gene expression. A recombinant vector may comprise an isolated scorpion venom toxin polypeptide transcriptional regulatory sequence, such as a promoter sequence, operably linked to sequences coding for a scorpion venom toxin polypeptide; or the transcriptional control sequences can be operably linked to coding sequences for a scorpion venom toxin fusion protein comprising scorpion venom toxin polypeptide fused to a polypeptide which facilitates detection. In these embodiments, the method comprises combining a candidate agent to be tested with a cell comprising a nucleic acid which comprises a scorpion venom toxin gene transcriptional regulatory element operably linked to a scorpion venom toxin polypeptide-coding sequence; and determining the effect of said agent on scorpion venom toxin polypeptide expression, which determination can be carried out by measuring an amount of scorpion venom toxin polypeptide mRNA, scorpion venom toxin polypeptide, or scorpion venom toxin fusion polypeptide produced by the cell.

Cell-based assays generally comprise the steps of contacting the cell with an agent to be tested, forming a test sample, and, after a suitable time, assessing the effect of the agent on scorpion venom toxin polypeptide expression. A control sample comprises the same cell without the candidate agent added. Scorpion venom toxin polypeptide expression levels are measured in both the test sample and the control sample. A comparison is made between scorpion venom toxin polypeptide expression level in the test sample and the control sample. Scorpion venom toxin polypeptide expression can be assessed using conventional assays. For example, when a mammalian cell line is transformed with a construct that results in expression of scorpion venom toxin polypeptide, scorpion venom toxin polypeptide mRNA levels can be detected and measured, as described above, or scorpion venom toxin polypeptide levels can be detected and measured, as described above. A suitable period of time for contacting the agent with the cell can be determined empirically, and is generally a time sufficient to allow entry of the agent into the cell and to allow the agent to have a measurable effect on scorpion venom toxin polypeptide mRNA and/or polypeptide levels. Generally, a suitable time is between 10 minutes and 24 hours, more typically about 1–8 hours. Methods of measuring scorpion venom toxin polypeptide mRNA levels are known in the art, several of which have been described above, and any of these methods can be used in the methods of the present invention to identify an agent which modulates scorpion venom toxin polypeptide mRNA level in a cell, including, but not limited to, a PCR, such as a PCR employing detectably labeled oligonucleotide primers, and any of a variety of hybridization assays. Similarly, scorpion venom toxin polypeptide levels can be measured using any standard method, several of which have been described herein, including, but not limited to, an immunoassay such as ELISA, for example an ELISA employing a detectably labeled antibody specific for a scorpion venom toxin polypeptide.

Preparation of Antivenom

Identification of potent components is an important first step in designing and obtaining effective antivenom. Antibodies raised against the critical toxic components have the potential to block the toxic effects and reduce the pain associated with the scorpion envenomation. Antibodies that specifically bind to scorpion venom toxin polypeptides are produced by: 1) immunization of non-human animals with the isolated cells and production of hybridomas; and 2) identification of antibodies that specifically bind scorpion venom toxin polypeptides (e.g., by screening hybridoma supernatants with scorpion venom toxin). Each of these steps is described below.

Antibodies specific to scorpion venom toxin polypeptides are produced by immunizing a non-human mammal (e.g., murine, rodentia, lagomorpha, ovine, porcine, bovine, etc.) with isolated scorpion venom toxin polypeptide. Immunization and hybridoma production with the scorpion venom toxin polypeptide can be accomplished according to conventional methods well known in the art. The immunized animal is an immunocompetent, non-human mammalian host, including murine, rodentia, lagomorpha, ovine, porcine, bovine, etc. is immunized with scorpion venom toxin polypeptide isolated as described above. The choice of a particular host is primarily one of convenience. Immunizations are generally performed in accordance with conventional techniques, where the isolated cells may be injected subcutaneously, intramuscularly, intraperitoneally, intravascularly, etc.

Normally, from about 106 to 108 cells, preferably about 107 cells, will be used, which may be divided up into 1 or more injections, usually not more than about 8 injections, over a period of from about one to three weeks. The injections may be with or without adjuvant, e.g. complete or incomplete Freund's adjuvant, specol, alum, etc.

Either monoclonal or polyclonal antibodies, preferably monoclonal antibodies (MAbs), are produced from the immunized animal. Polyclonal antisera may be harvested from serum in accordance with conventional methods after completion of the immunization schedule. For production of MAbs, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Methods for hybridoma production are well known in the art (see, e.g., Antibodies, A Laboratory Manual, Harlow & Lane eds., (1988) Cold Spring Harbor Press).

The antibodies and MAbs of the present invention can be modified in any of a variety of ways, with the proviso that the modified MAbs retain substantially specific binding to the original antigen (e.g., to the original scorpion venom toxin polypeptide). The ability of such modified antibodies to specifically and sensitively bind their original antigen can be assessed in in vitro assays as described herein (e.g., to assess binding of the modified antibodies to scorpion venom toxin in cytospin preparations, to scorpion venom toxin cell-specific polypeptides in ELISA assays, etc.). Such screening is routine and, with the guidance provided herein, within the skill of the ordinarily skilled artisan.

Modified antibodies contemplated by the present invention include those produced using biochemical, chemical, or recombinant DNA techniques. For example, antibody fragments, such as Fv, F(ab')2 and Fab may be prepared from the antibodies of the invention by cleavage of the intact protein, e.g., by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule. Preferably, such antibody fragments retain antigen avidity and/or affinity that is substantially the same as the original antibody from which they are derived.

The subject antibodies may also be produced as a single chain, instead of the normal multimeric structure. Single chain antibodies are described in Jost et al. (1994) J. Biol. Chem. 269:26267–73, and others. DNA sequences encoding the variable region of the heavy chain and the variable region of the light chain are ligated to a spacer encoding at least about four amino acids of small neutral amino acids, including glycine and/or serine. The protein encoded by this fusion allows assembly of a functional variable region that retains the specificity and affinity of the original antibody.

The antibodies of the invention may also be humanized. Methods of humanizing antibodies are well known in the art. The humanized antibody may be the product of an animal having transgenic human immunoglobulin (Ig) constant region genes (see for example, WO 90/10077 and WO 90/04036). Alternatively, the antibody of interest may be engineered by recombinant DNA techniques to substitute the CH1, CH2, CH3, hinge domains, and/or the framework residues with the corresponding human sequence (see WO 92/02190). Humanized antibodies are of particular interest for in vivo use in humans.

The antibodies of the present invention may also be used to produce chimeric antibodies. The use of Ig cDNA for construction of chimeric Ig genes is known in the art (Liu et al. (1987) Proc. Natl. Acad. Sci. 84:3439; Liu et al. (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91–3242. Human C region genes are readily available from known clones. The chimeric, humanized antibody is then expressed by conventional methods.

Expression vectors for use in modification of the antibodies of the invention are well known in the art and include plasmids, retroviruses, YACs, EBV derived episomes, and the like. For example, where the scorpion venom toxin-polypeptide antibody is to be modified to provide a human antibody heavy and/or light chain constant region, a convenient vector is one that encodes a functionally complete human CH or CL Ig sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Biol. 3:280), Rous sarcoma virus LTR (Gorman et al. (1982) Proc. Natl. Acad. Sci. 79:6777), and Moloney murine leukemia virus LTR (Grosschedl et al. (1985) Cell 41:885); native Ig promoters, etc.

Scorpion Venom Toxin Antivenom Preparation

The scorpion venom toxin polypeptide antivenom preparation is injected subcutaneously (intravenously or intramuscularly), at the site of the sting in a therapeutically effective amount. The preferred dose is 5 mL (50–75% scorpion venom toxin antiserum with suitable carrier), with a second 5 mL injection after 1–2 hours if no improvement. However, each dosage amount may range from 0.5 mL to 10 mL, depending on the recipient and the desired pharmacologic and/or physiologic effect.

The antivenom preparation may be administered with a suitable carrier. Carriers can be formulated in a pharmaceutical composition and can be used in methods of treatment of a subject. In the methods of the present invention, the compounds herein described in detail can form the active ingredient, and are typically administered in admixture with suitable pharmaceutical diluents, excipients, or carriers (collectively referred to herein as a pharmaceutically acceptable carrier or carrier materials) suitably selected with respect to the intended form of administration, and consistent with conventional pharmaceutical practices.

The carriers may be formulations at a pharmacologically effective dose in pharmaceutically acceptable media, for example normal saline, PBS, etc. The additives may include bactericidal agents, antihistamines, stabilizers, buffers, or the like. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Various methods for administration may be employed, and will vary according to a variety of factors, such as the agent to be delivered, the formulation used, route of delivery, the condition to be treated, and the like. The formulation may be injected intravascularly, subcutaneously, peritoneally, etc. The formulation may also be administered through a saline IV. The dosage of the therapeutic formulation will vary widely, depending upon the nature of the injury, the frequency of administration, the manner of administration, the clearance of the toxin from the host, and the like. The initial dose may be larger, followed by smaller booster doses. The dose may be administered as infrequently as one time, or fractionated into smaller doses and administered every hour, every two hours, every 6 hours, every 12 hours, etc.

The antitoxins may be administered as a combination therapy with other suitable pharmacologically active agents. The additional drugs may be administered separately or in conjunction with the peptide or antibody compositions, and may be included in the same formulation. For example, the agent can be administered with one or more compatible anti-inflammatory agents, analgesics, corticosteroids, and antihistamines.

In general, the antitoxin present in the therapeutic formulation is administered in an effective amount to provide for the desired effect in the subject treated. The terms "effective amount" and/or "therapeutic amount" means a dosage sufficient to provide treatment for the injury. This will vary depending on the patient, the injury and the treatment being effected.

Purified Scorpion Venom Toxin Preparation

The preparation of a purified scorpion venom toxin polypeptide may be injected directly into a subject suffering from a scorpion sting. The scorpion venom toxin polypeptide may be administered in a pharmaceutically suitable preparation subcutaneously (intravenously or intramuscularly) at the site of the sting in a therapeutically effective amount. The preferred dose is 5 mL (50–95% scorpion venom toxin polypeptide with suitable carrier), given one time. However, booster doses may be given after one hour if there is not sufficient relief of symptoms. The preferred dosage is 5 mL, however the range is from 1.0 mL to 10.0 mL depending on the recipient and the desired pharmacologic and/or physiologic effect.

Kits

The present invention also includes pharmaceutical kits useful, for example, for the treatment of scorpion stings, which comprise one or more containers containing a pharmaceutical composition comprising a therapeutically effective amount of a scorpion venom toxin polypeptide compound or antibody to a scorpion venom toxin polypeptide. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. In the present disclosure it should be understood that the specified materials and conditions are important in practicing the invention but that unspecified materials and conditions are not excluded so long as they do not prevent the benefits of the invention from being realized.

EXAMPLES

Example 1

Methods and Materials used in Purification and Characterization of Venom

Sample Preparation: Scorpion venom was obtained from captive *P. transvaalicus* scorpions by passing a small electric shock through the telson to contract the muscles. The venom was collected in a cryo tube as a pooled sample from three milkings at the SAVP (South African Vaccine Producers Ltd., South Africa) facilities, dried and sent to UC Davis. Dried venom was resuspended in sterile water at 10 mg/ml by vigorous vortexing and filtered through 0.45 μm filter.

Birtoxin HPLC Purification: Filtered venom sample was injected into a Vydac (Hesperia, Calif.) Reverse Phase C4 Analytical HPLC column (4.6 mm ID×25 mm Length) connected to a Hewlett-Packard HP 1100 system coupled to a diode array detector and a computer running CHEMSTATION® software. A gradient was formed with the following conditions: 5 to 65% solvent A in 60 minutes, 65% solvent A for another 20 minutes for a total of 80 minutes at a flow rate of 600 μl per minute (solvent A: 95% acetonitrile, 5% water, 0.1% TFA solvent B: 95% water, 5% acetonitrile, 0.1% TFA). Elution was monitored by following the UV traces at 214 and 280 nm. Fractions were collected manually into tubes pretreated with BSA (1 mg/mL) and washed with 1:1 acetonitrile/water, 1:1 methanol/water and water respectively. Biologically active fractions were further separated using a Michrome Magic 2002 Microbore HPLC system equipped with a RP C 18 column and an online 5 μpeptide trap (Michrome BioResources, Inc., Auburn, Calif.) with a linear gradient from 5% to 70% solvent A in 23 minutes at a flow rate of 50 μL/min. Fractions were collected manually into BSA pretreated tubes by following the UV trace.

Ikitoxin HPLC Purification: Birtoxin was purified as described above with the exception of the following modifications. The crude venom was resuspended in solvent A (2:98:1 ACN:H2O) and sonicated briefly until no precipitate is left. The venom was first injected into a Michrome Magic 2002 microbore HPLC system equipped with a C4 Magic Bullet (Michrome Bioresources, Auburn, Calif.) column (4 to 1 mm I.D.) and a 5 μl peptide trap. A gradient of 2–65% solvent B was generated over 15 minutes with a flow rate of 300 μL/min. UV absorbance trace was followed at 214 nm. Fraction P4 from multiple runs was collected and injected into a Michrome C18 RP-HPLC microbore column. The 15.3 min RT peak was collected and rerun on the same column to further purify the peptide. For ikitoxin fraction P3 of the C4 column was collected and injected into the same microbore C18 column running at 50 ml/min with a linear gradient of 3% solvent B/min increase for 23 minutes. The third major fraction was collected as ikitoxin and polished by rerunning on the same column.

Uctoxin HPLC Purification: Uctoxin was purified through three steps of RP-HPLC guided by insect and mouse bioassays. Initially the venom of P.transvaalicus was resuspended in solvent A (2% acetonitrile 98% water 0.1% TFA) and ran multiple times through a C4 magic bullet column hooked up to a Magic 2002 microbore HPLC System with a linear gradient of 2 to 65% solvent B (98% acetonitrile 2% water 0.1% TFA) in 15 minutes at a flow rate of 300 μL/min. as described above for ikitoxon. UV trace at 214 and 280 nm was monitored. Fraction P3 from the first column was collected, several runs were pooled and freeze dried. This fraction was run on a Michrom C18 microbore column on the same system with a linear gradient of 2 to 65% solvent B in 30 minutes at a flow rate of 50 μL/min. Peak 2 from the C18 column was further purified by running it through a microbore phenyl column on the same system with the same gradient conditions. Purity was confirmed using MALDI-TOF MS. Biological activity of peptide was monitored by intracerebroventricular injection of mice and also injections of blowfly and tobacco budworm larvae. For bioassays uctoxin was purified and resuspended in 20 mM ammonium acetate buffer with 1 ug/ul BSA. (The 50% effective doses (ED50) were determined according to Reed and Muench (Reed L. J., Muench, S. 1938 Am.J.Hyg 27, 493–497.))

Bioassays: Male Swiss-Webster mice were purchased from Charles River, Inc., and housed at the Animal Housing Facility, UC Davis. Blowfly (Sarcophaga spp.), crickets (*Acheta domesticus*) and Anole lizards (*Anoles caroliensis*) were purchased from Carolina Biologicals (Burlington, N.C.). Cotton bollworms (Heliothis virescens) were obtained from USDA/ARS (Stoneville, Mich.) and reared on artificial diet. Collected fractions were tested on mice by intracerebroventricular injections and by injecting last instar blowfly larvae. Third instar cotton bollworms and adult common house crickets were also used in screening for insecticidal components. Briefly, fractions were concentrated to dryness using a Heto Speed Vac (ATR, Inc. Emeryville, Calif.). Dried samples were resuspended in 10 µl 20 mM ammonium acetate buffer with 1 µg/µl BSA and incubated overnight at 4° C. to insure proper refolding before injection to the test animals. Mice were anesthetized using ethyl ether and intracerebroventricular injections of peptide solutions were executed immediately. Control animals injected with BSA in buffer did not show any symptoms when recovering from anesthesia. All symptoms were observed and recorded up to 24 hours post injection. All experiments were carried out in accordance with the guidelines laid down by the National Institutes of Health in the USA regarding the care and use of experimental animals.

Mass Spectroscopy: Mass spectra of crude venom, separated fractions and isolated peptide were analyzed off-line in a Biflex III (Bruker Daltonics, Bremen, Germany) MALDI-TOF instrument in positive ion mode. The instrument was equipped with a nitrogen laser operating at an output of 337.1 nm with a pulse width of 3 ns, and a repetition rate of 6 Hz. Experiments were conducted in reflector mode with an acceleration potential of 19.3 kV, a reflector potential of 20.0 kV, a time base of 2–4 ns, and a delay of 10–30 ms. The output signal of the detector was digitized at a sampling rate of 500 MHz/channel using a 1 GHz Lecroy digitizer. A camera mounted on a microscope facilitated inspecting the sample crystallization and selecting the largest crystals for analysis. External calibration was performed using angiotensin II (1046.53 Da), somatostatin 28 (3147.47 Da), and insulin (5808.6 Da). For analysis, matrix solutions consisting of sinapinic acid, 3,5-dimethoxy-4-hydroxycinnaminic acid, or α-cyano-4-hydroxycinnamic acid, were mixed in a 1:1 ratio with samples, spotted on the target and allowed to dry. MassLynx (Micromass UK Limited, Manchester, UK) software was used for data processing and analysis.

Edman Sequencing: Purity following HPLC was evaluated by MALDI-TOF as described. For amino acid sequence determination the cysteine residues of the peptide were reduced and carboxymethylated by incubating in 6 M guanidine hydrochloride, 0.1 M Tris-HCI (pH 8.3), 1 mM EDTA and 20 mM dithiothreitol for 1 hour at 37° C. Iodoacetic acid was then added to a final concentration of 50 mM and incubated for an additional hour at 37° C. in the dark. Finally 300 picomoles of peptide was subjected to automated Edman sequencing for 60 cycles using a Hewlett-Packard HP GS1000 Sequence Analyzer at the Molecular Structure Facility at UC Davis.

Peptide Quantification and Amino Acid Analysis: Amino acid analysis was conducted by the Molecular Structure Facility at UC Davis with standard methods using a Beckman 6300 Na citrate-based amino acid analyzer. Peptide quantification was accomplished after determination of the molecular mass, primary sequence and amino acid analysis. The extinction coefficient for birtoxin was calculated according to Gill et al. (1989) Anal. Biochem. 182:319–326). Calculation of protein extinction coefficients from amino acid sequence data using the following formula:

$$\Sigma 280 = 5690 * ntrp + 1280 * ntyr + 120 * nss \qquad \text{eq.(1)}.$$

Extinction coefficient for birtoxin was calculated as 13730 M-1cm-1. Σ280 for birtoxin was confirmed experimentally by utilizing the A280 and concentration of birtoxin determined by amino acid analysis according to Beer-Lambert law. Absorbance at 280 nm was determined using a Biorad SmartSpec 3000 Spectrophotometer using a quartz cuvette.

Structural Analysis: NMR structures for peptide toxins from Centruroides exelicauda, Centruroides sculpturatus and Centruroides noxius were downloaded from the ExPASy Molecular Biology Server in pdb format. The amino acid sequence of birtoxin was aligned and the backbone atoms were overlaid on the NMR resolved 3D structures using the Swiss PDB Viewer software's magic fit and improve fit functions sequentially. Peptide Tools from the ExPASy Molecular Biology Server was used for mass calculation of sequenced peptide. Sequence homologies were determined using the ClustalW program at the EMBL European Bioinformatic Institute server. Sequence alignments were visualized using the EsPriPt tool at the ExPASy Molecular Biology Server.

Binding Assays: Binding of uctoxin and birtoxin to rat brain synaptosomes was measured by utilizing the ability of site 3 toxins to enhance the binding of batrachotoxin according to Catterall (J. Biol. Chem. 1981 256:8922–8927). Rat brain synaptosomes were prepared from two Springer-Dowley male rats according to Catterall (J. Biol. Chem. 1981 256:8922–8927). Briefly cortex from rat brain was excised and homogenized thoroughly using a glass homogenizer. The homogenate was centrifuged for 1 hr., pelleted, and resuspended in binding buffer and frozen at −80° C. in aliquots of 60 µl. Rat brain synaptosomes (300 µg/mL) were suspended in 250 µL of binding buffer with 25 nM [3H] BTX-A (NEN) as described by Catterall (J. Biol. Chem. 1981 256:8922–8927). The reaction was incubated for 50 min at 37° C. and terminated by filtering and washing with cold wash buffer. Non-specific binding was determined in the presence of 300 uM veratridine (Calbiochem).

Example 2

Characterization of Venom

The mass profile of the crude venom using MALDI-TOF was initially determined. Mass spectroscopy of the crude venom resulted in detection of 72 components within the mass range of 750 to 7500 Da. See Table 2, below.

TABLE 1

| reaction | Mouse (IC injection) | Blow fly/H. virescens larvae | Molecular Ion Masses Detected (M + H) + |
|---|---|---|---|
| 0 | + | −/− | None Detected above 2000 Da |
| P1 | + | −/− | None Detected above 2000 Da |
| P2 | − | +++/− | 3492, 3640, 3769, 3912, 4092a, 4297, 4512, |
| PreP3 | ++ | −/− | Not determined |
| P3 | +++ | +++/− | 5757, 6544a, 6615a, 6635, 7221, 7215, 7261 |
| P4 | ++ | −/− | 2437, 5258, 5441, 5648, 6057, 6356, 6526, 6543a, 6574 |
| P5 | +++ | −/− | 5543, 5752, 6160, 6643a, 6854, 7225, 7303 |
| P6 | ++ | −/− | 6603a |
| P7 | +++ | −/− | None Detected above 2000 Da |

TABLE 1-continued

| reaction | Mouse (IC injection) | Blow fly/H. virescens larvae | Molecular Ion Masses Detected (M + H) + |
|---|---|---|---|
| P8 Venom | + LD99 is 4.8 µg crude venom/ 20 gr mouse | –/– LD99 for Blowfly is 1.2 µg venom/100 mg larvae | Not determined |

<sup>a</sup> Most abundant species

The purification procedure began by applying the water solubilized crude venom directly into a C4 Reverse Phase column equipped with a C4 guard column. Optimization of the gradient conditions resulted in consistent separation of the venom into 10 fractions (FIG. 1). Soluble crude venom and each of the fractions were tested for activity against mice, three insect species, and anole lizards (Table 1, above). As shown in Table 1, fractions P0, P1, P2, P3, P3, P4, P5 and P6 had activity against mice and fractions P2 and P3 had activity against blowfly larvae. Fraction P2 was specific for blowfly only. Interestingly, the crude venom had limited toxicity against insects.

The material between the above peaks was collected and assayed; however, it showed little biological activity. The LD99 for common house cricket and bollworm were well above 48 µg/insect for the crude venom. On the contrary, the venom was quite potent against mice with an LD99 of 4.8 µg crude venom/20 g. mouse with intracerebroventricular injection. Venom was at least five times less toxic when injected subcutaneously and fifty times less toxic when injected intraperitoneally. The crude venom did not show noticeable activity towards adult Anolis lizards when injected subcutaneously at even high doses (100 µg venom/10 g lizard) except for slowing their motion temporarily for about 3 minutes.

Example 3

Purification and Characterization of Birtoxin

Fraction P4 (FIG. 1) from the C4 column caused severe symptoms when injected to mice. The injected mice were first stunned, then started to tremble, and the tremors severity increased with time and lasted up to 24 hours. Also the paws were contracted and the body took the shape of hunchback with frequent whole body jerks. The symptoms did not initiate immediately after the injection was completed but increased in intensity for half an hour after a 10-minute lag. Control animals recovered within three minutes. From the UV absorbance of the C4 column profile birtoxin was estimated to constitute 12–14% of the crude venom. Fraction P4 was further purified from the first column by combining three batches and then injecting into a C18 Microbore column. Toxicity was only seen in the UV dense fraction collected from the microbore run. This second step resulted in more than 97% purity as determined by MALDI-TOF (FIG. 2). This fraction was also injected to mice and biological activity was confirmed. Injection of 1 µg of pure birtoxin induced severe neurotoxic symptoms in mice up to 24 hours but was not lethal. However, 2 µg of pure peptide was lethal.

Example 4

Birtoxin Sequence Determination

The peptide was then reduced, carboxymethylated and the amino acid sequence was determined as described. The mass for native birtoxin is determined to be 6543.6 Da using MALDI-TOF. Amino acid sequencing resulted in 56 amino acids, which totaled a calculated mass of 6438.2 Da. Serine 57 was not detected by Edman degradation due to the low conversion efficacy and low amount of peptide left on the column, but Valine 58 was detected clearly. Amino acid analysis revealed the presence of an extra Serine, which was assigned to position 57. The calculated and expected mass was in concert after assigning the 57th amino acid as a Serine residue. The presence of six cysteine residues was confirmed by measuring the molecular mass of reduced and carboxymethylated birtoxin (FIG. 2b). Thus, the sequence was determined to be:

ADVPGNYPLDKDGNTYKCFLLGGNEE-
CLNVCKLHGVQYGYCYASKCWCEY    LEDDKDVS
(SEQ ID NO:1) A homology search revealed over 40 matches of scorpion toxins with percent identity ranging from 57% to 22%. The best of the matches were selected for multiple sequence alignment (FIG. 3; see also Brief Description of FIG. 3 above). Birtoxin shows significant identity to the previously discovered sodium channel blocker toxins from the scorpions C. exilicauda, Centruroides sulcatus, C. sculpturatus, and C. noxius.

Example 5

Birtoxin Structural Analysis

Birtoxin structure was compared to similar structures (Lee, W. et al. (1994) Biochemistry 33:2468–2475; Jablonsky, M. J. et al. (1995) J. Mol. Biol. 248:449–458; Pintar, A. et al. (1999) J. Mol. Biol. 287:359–367). The Swiss PDB Viewer Software was used to visualize the downloaded pdb format structures and align and overlay the birtoxin sequence to the NMR resolved structures. The backbone overlay of birtoxin on CeNV1 structure (FIG. 4a) resulted in good agreement between the two backbones (calculated RMS of 0.01 Å between the two aligned backbones). Thus, the positions of the four disulfides in the CeNV1 toxin with respect to the three disulfides in birtoxin were visualized. The aligned structure revealed that both toxins have a conserved core with three disulfide bridges (FIG. 4b). In the CeNVI cysteines 16–41, 25–46 and 29–48 are disulfide bridged and form the core disulfides, whereas in birtoxin all disulfide bridges are at the core. CeNV1 has a fourth disulfide bridge between cys12 and cys65 (FIG. 4a). This fourth disulfide is, like the other three, very well conserved among the LCN peptide toxin family (FIG. 3). Birtoxin does not possess an equivalent for cys12 and does not possess the 9–13 residues at the C-terminus of CeNV1, CsN-3 and CnN2. The NMR structure reveals that the fourth disulfide wraps the N and C termini from the outside of the molecule (FIG. 4). This was named the "wrapper" disulfide. The absence of two cysteine residues in birtoxin corresponding to Cys12 and Cys65 in CeNV1 and other LCNs indicates the absence of the fourth disulfide. Therefore, birtoxin has a novel structural organization and an alternative system for keeping the polypeptide chain in a particular three-dimensional confirmation that retains biological activity without the fourth disulfide bridge.

Example 6

Purification and Characterization of Ikitoxin

The magic bullet C4 column gave the exact separation as obtained by a Vydac analytical C4 column in one fourth of the running time. Birtoxin and ikitoxin were well separated on the C4 column whereas they had a similar retention time on the C18 column. Injection of fractions P3, P4 and a mixture of both on a C18 microbore column (FIG. 5) illustrates that the two peptides could not be resolved on a C18 column. Moreover, injection of pure ikitoxin together with birtoxin in equal quantity to the C18 column resulted in a broad peak as observed for partially purified peaks. However, the two peptides elute in different fractions when crude venom is run through a C4 column. The composition of fractions P3, P4 and their mixture were evaluated using mass spectroscopy (MS). The MS results indicated the presence of the species 6543 and 6615 in fraction P3 and presence of only 6543 in fraction P4. Therefore, the 6615 Da species was purified by first separating the C4 fractions and then running smaller quantities of the C4–P3 fraction on the C18 column multiple times until the previously broad major peaks were sharp and shoulder peaks disappeared. Purity was confirmed with MS.

EXAMPLE 7

Comparison of Ikitoxin and Birtoxin Bioactivity

Next, the biological activities of Ikitoxin and Birtoxin were compared. Mouse biological activity was evaluated by intracerebroventricular injections of 7–8 week old male Swiss-Webster mice using 0.2–1 mg purified toxin. Mice injected with birtoxin showed typical neurotoxicity symptoms as previously described for birtoxin comprising of convulsions, tremors, increased heart rate and finally death. Injection of ikitoxin in equal quantities resulted in an unusual effect. The animals did not show any tremors or any of the symptoms of birtoxin. Instead the ikitoxin injected mice contracted periodic unprovoked jumps with an initial frequency of about 3 jumps per minute for 20 minutes. Within three hours of injection the symptom gradually faded and the mice were normal afterwards. Ikitoxin did not show lethality during the course of the observation period in the range of injected doses.

Activity against insects was tested by injecting blowfly and tobacco budworm larvae. Injections of both toxins to insects did not show any noticeable effect at high doses.

Example 8

Ikitoxin Sequence Determination and Characterization

The 6615 Da ikitoxin species was then submitted Edman sequencing and the complete amino acid sequencing of ikitoxin was determined to be:

ADVPGNYPLDKDGNTYKCFLLGENEE-CLNVCKLHGVQYGYCYASKCWCEY LEDDKDVS (SEQ ID NO:2). The only difference from birtoxin is at the 23rd residue, which is a glycine in birtoxin and a glutamic acid residue in ikitoxin. This difference of gly23 to glu23 also corresponded with a 72 Da shift in mass for ikitoxin as compared to birtoxin.

The profound differences of symptoms prompted an examination of the effect Gly23 to Glu23 change at the molecular level. As seen in FIG. 8, the alpha helix region of birtoxin was modeled according to an NMR determined structure of CeNV1 as described above for birtoxin. According to the model the region where gly23 resides on birtoxin appears to be solvent accessible. This is supported by the fact that the single amino acid substitution alters the biological activity. The surface potential calculation presentation (FIG. 8) also indicates a significant structural difference where the region preceding the alpha helix is transformed from a neutral patch to an acidic domain.

Example 9

Uctoxin Purification

Fraction P3 from the C4 column displayed both potent insecticidal and potent anti-mammal activity at even low doses. Peak 3 then separated into two major peaks on the C18 microbore column. Injection of these peaks into Sarcophaga larvae resulted in bioactivity only in the case of the first major peak, which contained uctoxin. The second peak contained ikitoxin and was not active against Sarcophaga. These two peaks were collected separately and re-run on the same column using the same gradient conditions to remove the remaining ikitoxin. Purity of the uctoxin peak was confirmed with MALDI-MS. Uctoxin was sequenced as described above for birtoxin and ikitoxin. The deducted amino acid sequence mass agreed the MALDI determination. Sequence alignment of uctoxin to known alpha toxins revealed high level of identity, including the presence of four conserved disulfide bridges typical of toxins in its class.

Example 10

Uctoxin Bioactivity

The insecticidal activity of uctoxin was then characterized by Sarcophaga bioassays. Uctoxin caused immediate flaccid paralysis when injected to last instar Sarcophaga larvae. The ED50 of uctoxin was about 70 ng/100 mg larvae. Intracerebroventricular administration of uctoxin to mice resulted in consistent contraction and tremors. A formal determination of lethal dose was not undertaken but 0.5 µg of uctoxin caused lethality within 30 minutes, indicating the potency of this toxin.

Example 11

Rat Brain Synaptosome Binding Properties of Uctoxin and Birtoxin

We further characterized uctoxin and birtoxin by measuring the binding properties of the toxins to rat brain synaptosomes. Birtoxin has an EC50 (effective concentration) of about 5 nM and enhances the binding of [3H] BTX about 4.32 fold (FIG. 11). Whereas uctoxin is less potent with an EC50 of about 60 nM and an enhancement of 2 fold (FIG. 12).

Example 12

Ion Channel Binding Properties of Birtoxin

Additional studies of Birtoxin revealed that the toxin binds to sodium channel binding site 3 and blocks the sodium channel by prolonging the inactivation (preventing the closure of the channel) of the channel. The action of Birtoxin is similar to that for most of the known scorpion toxins that bind to sodium channel binding site 3.

Example 13

Isolation and Sequencing of Dortoxin, Bestoxin and Ikitoxin

Subsequent additional HPLC purification of the original HPLC fractions yielded an additional three toxins, dortoxin from fraction P5, bestoxin from fraction P6, and uctoxin from fraction P3. These toxins were purified by running the individual fractions on a C18 column as described above for ikitoxin. Dortoxin is the major component of fraction P5 and the C18 run of this fraction gave a large peak with front and hind shoulders. Contaminants were separated for each fraction by rerunning the major peak through the same column under the same conditions and collecting only the middle part (purest) of the fraction. This polishing step resulted in more than 97% purity. Purity using mass spectrometry, SDS-PAGE and IEF, as described above. The peptide was then subjected to Edman sequencing and partial amino acid sequences were determined. The amino acid sequence of dortoxin were determined to be:

ADVPGNYPLDKDGNTYTCLKLGENKDC-QKVCKLHGVQYGYCYAFECWCK EYLDDKDSV (SEQ ID NO:3). The amino acid sequence of bestoxin were determined to be:

ADVPGNYPLDKDGNTYTCLELGENKDC-QKVCKLHGVQYGYCYAFSCWCKE YLDDKDSV (SEQ ID NO:4). The first 43 amino acids of uctoxin were determined to be: KKDGYPVDHANCKYECWYNNVY-CNDLCKKLKANHGYCYGYNLA (SEQ ID NO:5).

Example 14

Bioactivity of Dortoxin, Bestoxin, and Ikitoxin

The biological activities of dortoxin, bestoxin, and ikitoxin were evaluated in blowfly larvae, tobacco budworm larvae, and mice. Blowfly larvae, tobacco budworm larvae were injected with 1 µL of fraction or toxin solution in water. The effects were observed and recorded up to 24 hrs post injection. The toxins to were also injected to mice (swiss-webster male 4–6 week old mice) through an intracerebroventricular route (brain). The mice were anesthetized using ethyl ether then injected with various doses of 5 µL of test solution. The effects were again observed and recorded up to 24 hrs post injection. Dortoxin was very toxic to mice (LD99<0.5 µg/20 gr of mouse) and caused convulsions, tremors and death. However, bestoxin showed a very different effect. Bestoxin caused the mice to contract, twist and roll around itself indefinitely. The experiments were terminated after 48 hrs of observation. At the end of 48 hrs the bestoxin-injected mice were still live, dessicated, and exhausted but still continued to roll. Bestoxin injected mice were hypersensitive to stimuli. Bestoxin is only two amino acid different from its sister peptide dortoxin. The MALDI determined molecular masses for dortoxin (6643 Da) and bestoxin (6603 Da) also agree with the two amino acid difference of Lys20 in dortoxin to Glu20 in bestoxin and Glu45 in dortoxin to Ser45 in bestoxin.

Example 15

Methods and Materials used in Purification and Characterization of Parakinins

The venom of the South African Scorpion Parabuthus transvaalicus was characterized by separation through a C18 reverse phase microbore column in a microbore HPLC connected to Ultima TOF mass spectrometer. The components with molecular masses of 986 Da and 972 Da were selected. Both peptides are very hydrophobic and were well retained in the column until 50% mobile phase. Once the retention times were determined using the LC-MS run, the crude venom was separated through an analytical C18 reverse phase column. The two peptides were well separated from each other using a simple linear gradient. The 986 Da species displayed a very high abundance compared to the 972 Da species. Both peptides were then subjected to a second step of HPLC purification this time using a microbore C18 RP column on a microbore HPLC system. Both peptides displayed similar retention times on the microbore column (eluting at about 50% mobile phase). These two steps give high purity (>95%) as determined by mass spectrometry.

Example 16

Characterization of Parakinins

Both peptides were initially submitted to amino acid analysis (table 2). The results show that the two peptides differ by a single amino acid residue, and isoleucine in 986 Da species is replaced by a valine in 972 Da species. This is in agreement with a molecular mass difference of 14 Da. Next, peptide 986 were submitted to Edman sequencing. However, despite the high quantity of the initial material only four amino acids -xVPPFx- are detected. This blockage is later confirmed by the lack of sequence when peptide 972 is submitted to Edman sequencing. Both peptides are then subjected to MS-MS fragmentation. This experiment resulted with a partial sequence as shown in the table. Therefore we subjected the more abundant 986 Da species to NMR. The structure of parakinin-1 was then resolved by a combination of all four techniques shown in table 2. The sequence of parakinin-2 therefore was assigned with a single amino acid difference. Parakinins have a modification at the N-terminus consisting of a modified proline residue. This is the first example of a unique post-translational modification.

TABLE 2

| Method | Sequence obtained for Parakinin-1 (986 Da) | Sequence obtained for Parakinin-2 (972 Da) |
| --- | --- | --- |
| AAA | 2 PHE, 1 ARG, 1 ILE, 1 VAL, 2 PRO | 2 PHE, 1 ARG, 2 VAL, 2 PRO |
| Edman | N-XVPPFX | No sequence obtained |
| MS—MS | FIVPPFR | FVVPPFR |
| NMR | mPFIVPPFR | Mpfvvppfr (deduced) |

Table 2 shows the structure determination of parakinins. A combination of four methods is employed for the sequencing of these peptides. Amino acid analysis revealed the identity and stoichiometry of amino acids present in these peptides. Edman sequencing showed that both peptides were n-terminally blocked. MS-MS fragmentation revealed a partial sequence which is confirmed and completed by nuclear magnetic resonance. m denotes modification.

The preliminary biological activity of parakinins I investigated by in vivo assays conducted on insects and mice. The results are presented in table 3. Parakinins are active and potent against both invertebrates and vertebrates. These in vivo effects implicate potential pharmaceutical use and development. Due to the small nature of parakinins analogs of these peptides can be synthesized and tested very rapidly. Therefore quantitative structure-activity relationships can be studied and more potent or more stable analogs can be obtained through conventional peptide synthesis and QSAR.

TABLE 3

| Test Organism | Parakinin-1 (986 Da) | Parakinin-2 (972 Da) |
|---|---|---|
| Insect blowfly | Contractive paralysis | Not determined |
| Insect Lepidoptera | Contractive paralysis | Not determined |
| Mouse (IC) low dose | Hyperventilation, Hyperactivity | Hyperventilation, Hyperactivity |
| Mouse (IC) high dose | Paralysis | Paralysis |
| Mouse (SC) | Hyperventilation, Hyperactivity | Hyperactivity |

Table 3 shows the biological activity of parakinins.

The results show that the two peptides differ by a single amino acid residue, an isoleucine in the 986 Da species is replaced by a valine in the 972 species, which is in agreement with a molecular mass difference of 14 Da. These molecules are biologically active in many animal species, for example mice and insects.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A composition comprising a purified peptide of up to 25 amino acids comprising a sequence of at least 6 contiguous amino acids of any one of SEQ IDs NOs:27–30, wherein said peptide has a physiological effect when administered to a mammal.

2. The composition of claim 1, wherein said peptide comprises an amino acid sequence of eight contiguous amino acids that is at least 80% identical to the amino acid sequence of any one of SEQ IDs NOs:27–30.

3. The composition of claim 1 wherein the peptide is purified from the venom of *Parabuthus transvaalicus*.

4. A composition comprising a purified peptide of up to 25 amino acids wherein said peptide comprises the amino acid sequence of any one of SEQ IDs NOs:27–30 and wherein said peptide has a physiological effect when administered to a mammal.

5. A formulation comprising the composition of claim 1 or claim 4 and a pharmaceutically acceptable salt.

6. A method for altering a physiological response of an insect comprising contacting an insect with a composition of claim 1 or claim 4.

7. A method for altering a physiological response of a pest comprising contacting a pest with a composition of claim 1 or claim 4.

8. A composition comprising a purified, synthetically made, nonapeptide or octapeptide comprising a sequence of at least 6 contiguous amino acids of any one of SEQ IDs NOs:27–30, wherein said nonapeptide has a physiological effect when administered to a mammal.

9. The composition of claim 8, wherein said nonapeptide or octapeptide has an amino acid sequence at least 80% identical to the amino acid sequence of any one of SEQ IDs NOs:27–30.

10. A composition comprising a purified, synthetically made, nonapeptide or octapeptide having the amino acid sequence of any one of SEQ IDs NOs:27–30, wherein said peptide has a physiological effect when administered to a mammal.

11. A formulation comprising the composition of claim 8 or claim 10 and a pharmaceutically acceptable salt.

12. A method for altering a physiological response of an insect comprising contacting an insect with a composition of claim 8 or claim 10.

13. A method for altering a physiological response of a pest comprising contacting a pest with a composition of claim 8 or claim 10.

* * * * *

```
                         SEQUENCE LISTING

<160> NUMBER OF SEQ ID NOS: 30

<210> SEQ ID NO 1
<211> LENGTH: 58
<212> TYPE: PRT
<213> ORGANISM: Parabuthus transvaalicus

<400> SEQUENCE: 1

Ala Asp Val Pro Gly Asn Tyr Pro Leu Asp Lys Asp Gly Asn Thr Tyr
 1               5                  10                  15

Lys Cys Phe Leu Leu Gly Gly Asn Glu Glu Cys Leu Asn Val Cys Lys
                20                  25                  30

Leu His Gly Val Gln Tyr Gly Tyr Cys Tyr Ala Ser Lys Cys Trp Cys
            35                  40                  45

Glu Tyr Leu Glu Asp Asp Lys Asp Val Ser
        50                  55

<210> SEQ ID NO 2
<211> LENGTH: 58
<212> TYPE: PRT
<213> ORGANISM: Parabuthus transvaalicus

<400> SEQUENCE: 2

Ala Asp Val Pro Gly Asn Tyr Pro Leu Asp Lys Asp Gly Asn Thr Tyr
 1               5                  10                  15

Lys Cys Phe Leu Leu Gly Glu Asn Glu Glu Cys Leu Asn Val Cys Lys
                20                  25                  30

Leu His Gly Val Gln Tyr Gly Tyr Cys Tyr Ala Ser Lys Cys Trp Cys
            35                  40                  45

Glu Tyr Leu Glu Asp Asp Lys Asp Val Ser
        50                  55

<210> SEQ ID NO 3
<211> LENGTH: 58
<212> TYPE: PRT
<213> ORGANISM: Parabuthus transvaalicus

<400> SEQUENCE: 3

Ala Asp Val Pro Gly Asn Tyr Pro Leu Asp Lys Asp Gly Asn Thr Tyr
 1               5                  10                  15
```

```
Thr Cys Leu Lys Leu Gly Glu Asn Lys Asp Cys Gln Lys Val Cys Lys
         20                  25                  30

Leu His Gly Val Gln Tyr Gly Tyr Cys Tyr Ala Phe Glu Cys Trp Cys
         35                  40                  45

Lys Glu Tyr Leu Asp Asp Lys Asp Ser Val
     50                  55
```

<210> SEQ ID NO 4
<211> LENGTH: 58
<212> TYPE: PRT
<213> ORGANISM: Parabuthus transvaalicus

<400> SEQUENCE: 4

```
Ala Asp Val Pro Gly Asn Tyr Pro Leu Asp Lys Asp Gly Asn Thr Tyr
 1               5                  10                  15

Thr Cys Leu Glu Leu Gly Glu Asn Lys Asp Cys Gln Lys Val Cys Lys
         20                  25                  30

Leu His Gly Val Gln Tyr Gly Tyr Cys Tyr Ala Phe Ser Cys Trp Cys
         35                  40                  45

Lys Glu Tyr Leu Asp Asp Lys Asp Ser Val
     50                  55
```

<210> SEQ ID NO 5
<211> LENGTH: 43
<212> TYPE: PRT
<213> ORGANISM: Parabuthus transvaalicus

<400> SEQUENCE: 5

```
Lys Lys Asp Gly Tyr Pro Val Asp His Ala Asn Cys Lys Tyr Glu Cys
 1               5                  10                  15

Trp Tyr Asn Asn Val Tyr Cys Asn Asp Leu Cys Lys Lys Leu Lys Ala
         20                  25                  30

Asn His Gly Tyr Cys Tyr Gly Tyr Asn Leu Ala
         35                  40
```

<210> SEQ ID NO 6
<211> LENGTH: 61
<212> TYPE: PRT
<213> ORGANISM: Buthacus arenicola

<400> SEQUENCE: 6

```
Asp Gly Tyr Ile Arg Arg Arg Asp Gly Cys Lys Val Ser Cys Leu Phe
 1               5                  10                  15

Gly Asn Glu Gly Cys Asp Lys Glu Cys Lys Ala Tyr Gly Gly Ser Tyr
         20                  25                  30

Gly Tyr Cys Trp Thr Trp Gly Leu Ala Cys Trp Cys Glu Gly Leu Pro
         35                  40                  45

Asp Asp Lys Thr Trp Lys Ser Glu Thr Asn Thr Cys Gly
     50                  55                  60
```

<210> SEQ ID NO 7
<211> LENGTH: 61
<212> TYPE: PRT
<213> ORGANISM: Buthus occitanus

<400> SEQUENCE: 7

```
Asp Gly Tyr Ile Arg Arg Arg Asp Gly Cys Lys Val Ser Cys Leu Phe
 1               5                  10                  15

Gly Asn Glu Gly Cys Asp Lys Glu Cys Lys Ala Tyr Gly Gly Ser Tyr
         20                  25                  30
```

```
Gly Tyr Cys Trp Thr Trp Gly Leu Ala Cys Trp Cys Glu Gly Leu Pro
            35                  40                  45
Asp Asp Lys Thr Trp Lys Ser Glu Thr Asn Thr Cys Gly
 50                  55                  60
```

<210> SEQ ID NO 8
<211> LENGTH: 61
<212> TYPE: PRT
<213> ORGANISM: Buthus occitanus

<400> SEQUENCE: 8

```
Asp Gly Tyr Ile Arg Lys Arg Asp Gly Cys Lys Val Ser Cys Leu Phe
  1               5                  10                  15
Gly Asn Glu Gly Cys Asp Lys Glu Cys Lys Ala Tyr Gly Gly Ser Tyr
                 20                  25                  30
Gly Tyr Cys Trp Thr Trp Gly Leu Ala Cys Trp Cys Glu Gly Leu Pro
            35                  40                  45
Asp Asp Lys Thr Trp Lys Ser Glu Thr Asn Thr Cys Gly
 50                  55                  60
```

<210> SEQ ID NO 9
<211> LENGTH: 61
<212> TYPE: PRT
<213> ORGANISM: Leiurus quinquestriatus quinquestriatus

<400> SEQUENCE: 9

```
Asp Gly Tyr Ile Arg Lys Arg Asp Gly Cys Lys Leu Ser Cys Leu Phe
  1               5                  10                  15
Gly Asn Glu Gly Cys Asn Lys Glu Cys Lys Ser Tyr Gly Gly Ser Tyr
                 20                  25                  30
Gly Tyr Cys Trp Thr Trp Gly Leu Ala Cys Trp Cys Glu Gly Leu Pro
            35                  40                  45
Asp Glu Lys Thr Trp Lys Ser Glu Thr Asn Thr Cys Gly
 50                  55                  60
```

<210> SEQ ID NO 10
<211> LENGTH: 87
<212> TYPE: PRT
<213> ORGANISM: Centruroides noxius

<400> SEQUENCE: 10

```
Met Asn Ser Leu Leu Met Ile Thr Ala Cys Leu Val Leu Phe Gly Thr
  1               5                  10                  15
Val Trp Ala Lys Glu Gly Tyr Leu Val Asn Lys Ser Thr Gly Cys Lys
                 20                  25                  30
Tyr Gly Cys Phe Trp Leu Gly Lys Asn Glu Gly Cys Asp Lys Glu Cys
            35                  40                  45
Lys Ala Lys Asn Gln Gly Gly Ser Tyr Gly Tyr Cys Tyr Ala Phe Gly
 50                  55                  60
Cys Trp Cys Glu Gly Leu Pro Glu Ser Thr Pro Thr Tyr Pro Leu Pro
 65                  70                  75                  80
Asn Lys Thr Cys Ser Lys Lys
                 85
```

<210> SEQ ID NO 11
<211> LENGTH: 66
<212> TYPE: PRT
<213> ORGANISM: Centruroides limpidus limpidus -continued

```
<400> SEQUENCE: 11

Lys Glu Gly Tyr Leu Val Asn Lys Ser Thr Gly Cys Lys Tyr Gly Cys
1               5                   10                  15

Phe Trp Leu Gly Lys Asn Glu Asn Cys Asp Lys Glu Cys Lys Ala Lys
            20                  25                  30

Asn Gln Gly Gly Ser Tyr Gly Tyr Cys Tyr Ser Phe Ala Cys Trp Cys
        35                  40                  45

Glu Gly Leu Pro Glu Ser Thr Pro Thr Tyr Pro Leu Pro Asn Lys Ser
    50                  55                  60

Cys Ser
65

<210> SEQ ID NO 12
<211> LENGTH: 87
<212> TYPE: PRT
<213> ORGANISM: Centruroides noxius

<400> SEQUENCE: 12

Met Asn Ser Leu Leu Met Ile Thr Ala Cys Leu Phe Leu Ile Gly Thr
1               5                   10                  15

Val Trp Ala Lys Glu Gly Tyr Leu Val Asn Lys Ser Thr Gly Cys Lys
            20                  25                  30

Tyr Gly Cys Leu Leu Leu Gly Lys Asn Glu Gly Cys Asp Lys Glu Cys
        35                  40                  45

Lys Ala Lys Asn Gln Gly Gly Ser Tyr Gly Tyr Cys Tyr Ala Phe Gly
    50                  55                  60

Cys Trp Cys Glu Gly Leu Pro Glu Ser Thr Pro Thr Tyr Pro Leu Pro
65                  70                  75                  80

Asn Lys Ser Cys Ser Lys Lys
            85

<210> SEQ ID NO 13
<211> LENGTH: 65
<212> TYPE: PRT
<213> ORGANISM: Centruroides sculpturatus

<400> SEQUENCE: 13

Lys Glu Gly Tyr Leu Val Lys Lys Ser Asp Gly Cys Lys Tyr Asp Cys
1               5                   10                  15

Phe Trp Leu Gly Lys Asn Glu His Cys Asn Thr Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65

<210> SEQ ID NO 14
<211> LENGTH: 65
<212> TYPE: PRT
<213> ORGANISM: Centruroides sculpturatus

<400> SEQUENCE: 14

Lys Glu Gly Tyr Leu Val Lys Lys Ser Asp Gly Cys Lys Tyr Gly Cys
1               5                   10                  15

Leu Lys Leu Gly Glu Asn Glu Gly Cys Asp Thr Glu Cys Lys Ala Lys
            20                  25                  30
```

```
Asn Gln Gly Gly Ser Tyr Gly Tyr Cys Tyr Ala Phe Ala Cys Trp Cys
            35                  40                  45

Glu Gly Leu Pro Glu Ser Thr Pro Thr Tyr Pro Leu Pro Asn Lys Ser
 50                  55                  60

Cys
 65

<210> SEQ ID NO 15
<211> LENGTH: 66
<212> TYPE: PRT
<213> ORGANISM: Centruroides sculpturatus

<400> SEQUENCE: 15

Lys Glu Gly Tyr Leu Val Asn Lys Ser Thr Gly Cys Lys Tyr Gly Cys
 1               5                  10                  15

Leu Lys Leu Gly Glu Asn Glu Gly Asn Lys Cys Glu Cys Lys Ala Lys
            20                  25                  30

Asn Gln Gly Gly Ser Tyr Gly Tyr Cys Tyr Ala Phe Ala Cys Trp Cys
            35                  40                  45

Glu Gly Leu Pro Glu Ser Thr Pro Thr Tyr Pro Leu Pro Asn Lys Cys
 50                  55                  60

Ser Ser
 65

<210> SEQ ID NO 16
<211> LENGTH: 65
<212> TYPE: PRT
<213> ORGANISM: Centruroides noxius

<400> SEQUENCE: 16

Lys Glu Gly Tyr Leu Val Asn Ser Tyr Thr Gly Cys Lys Tyr Glu Cys
 1               5                  10                  15

Leu Lys Leu Gly Asp Asn Asp Tyr Cys Leu Arg Glu Cys Arg Gln Gln
            20                  25                  30

Tyr Gly Lys Ser Gly Gly Tyr Cys Tyr Ala Phe Ala Cys Trp Cys Thr
            35                  40                  45

His Leu Tyr Glu Gln Ala Val Val Trp Pro Leu Pro Asn Lys Thr Cys
 50                  55                  60

Asn
 65

<210> SEQ ID NO 17
<211> LENGTH: 66
<212> TYPE: PRT
<213> ORGANISM: Centruroides suffusus suffusus

<400> SEQUENCE: 17

Lys Glu Gly Tyr Leu Val Ser Lys Ser Thr Gly Cys Lys Tyr Glu Cys
 1               5                  10                  15

Leu Lys Leu Gly Asp Asn Asp Tyr Cys Leu Arg Glu Cys Lys Gln Gln
            20                  25                  30

Tyr Gly Lys Ser Ser Gly Gly Tyr Cys Tyr Ala Phe Ala Cys Trp Cys
            35                  40                  45

Thr His Leu Tyr Glu Gln Ala Val Val Trp Pro Leu Pro Asn Lys Thr
 50                  55                  60

Cys Asn
 65
```

```
<210> SEQ ID NO 18
<211> LENGTH: 84
<212> TYPE: PRT
<213> ORGANISM: Centruroides noxius

<400> SEQUENCE: 18

Leu Leu Ile Ile Thr Ala Cys Leu Ala Leu Ile Gly Thr Val Trp Ala
1               5                   10                  15

Lys Glu Gly Tyr Leu Val Asp Lys Asn Thr Gly Cys Lys Tyr Glu Cys
            20                  25                  30

Leu Lys Leu Gly Asp Asn Asp Tyr Cys Leu Arg Glu Cys Lys Gln Gln
        35                  40                  45

Tyr Gly Lys Gly Ala Gly Gly Tyr Cys Tyr Ala Phe Ala Cys Trp Cys
    50                  55                  60

Thr His Leu Tyr Glu Gln Ala Ile Val Trp Pro Leu Pro Asn Lys Arg
65                  70                  75                  80

Cys Ser Gly Lys

<210> SEQ ID NO 19
<211> LENGTH: 66
<212> TYPE: PRT
<213> ORGANISM: Centruroides limpidus tecomanus

<400> SEQUENCE: 19

Lys Glu Gly Tyr Leu Val Asn His Ser Thr Gly Cys Lys Tyr Glu Cys
1               5                   10                  15

Phe Lys Leu Gly Asp Asn Asp Tyr Cys Leu Arg Glu Cys Arg Gln Gln
            20                  25                  30

Tyr Gly Lys Gly Ala Gly Gly Tyr Cys Tyr Ala Phe Gly Cys Trp Cys
        35                  40                  45

Thr His Leu Tyr Glu Gln Ala Val Val Trp Pro Leu Pro Asn Lys Thr
    50                  55                  60

Cys Ser
65

<210> SEQ ID NO 20
<211> LENGTH: 66
<212> TYPE: PRT
<213> ORGANISM: Centruroides limpidus limpidus

<400> SEQUENCE: 20

Lys Glu Gly Tyr Ile Val Asn Leu Ser Thr Gly Cys Lys Tyr Glu Cys
1               5                   10                  15

Tyr Lys Leu Gly Asp Asn Asp Tyr Cys Leu Arg Glu Cys Lys Gln Gln
            20                  25                  30

Tyr Gly Lys Gly Ala Gly Gly Tyr Cys Tyr Ala Phe Gly Cys Trp Cys
        35                  40                  45

Thr His Leu Tyr Glu Gln Ala Val Val Trp Pro Leu Pro Lys Lys Thr
    50                  55                  60

Cys Thr
65

<210> SEQ ID NO 21
<211> LENGTH: 66
<212> TYPE: PRT
<213> ORGANISM: Centruroides noxius

<400> SEQUENCE: 21
```

```
Lys Glu Gly Tyr Leu Val Glu Leu Gly Thr Gly Cys Lys Tyr Glu Cys
 1               5                  10                  15
Phe Lys Leu Gly Asp Asn Asp Tyr Cys Leu Arg Glu Cys Lys Ala Arg
                20                  25                  30
Tyr Gly Lys Gly Ala Gly Gly Tyr Cys Tyr Ala Phe Gly Cys Trp Cys
            35                  40                  45
Thr Gln Leu Tyr Glu Gln Ala Val Val Trp Pro Leu Lys Asn Lys Thr
        50                  55                  60
Cys Arg
65
```

<210> SEQ ID NO 22
<211> LENGTH: 86
<212> TYPE: PRT
<213> ORGANISM: Centruroides noxius

<400> SEQUENCE: 22

```
Met Asn Ser Leu Leu Ile Ile Thr Ala Cys Leu Val Leu Ile Gly Thr
 1               5                  10                  15

Val Trp Ala Lys Asp Gly Tyr Leu Val Asp Val Lys Gly Cys Lys Lys
                20                  25                  30

Asn Cys Tyr Lys Leu Gly Glu Asn Asp Tyr Cys Asn Arg Glu Cys Lys
            35                  40                  45

Met Lys His Arg Gly Gly Ser Tyr Gly Tyr Cys Tyr Gly Phe Gly Cys
        50                  55                  60

Tyr Cys Glu Gly Leu Ser Asp Ser Thr Pro Thr Trp Pro Leu Pro Asn
65                  70                  75                  80

Lys Arg Cys Gly Gly Lys
                85
```

<210> SEQ ID NO 23
<211> LENGTH: 86
<212> TYPE: PRT
<213> ORGANISM: Centruroides noxius

<400> SEQUENCE: 23

```
Met Asn Ser Leu Leu Met Ile Thr Ala Cys Phe Val Leu Ile Gly Thr
 1               5                  10                  15

Val Trp Ala Lys Asp Gly Tyr Leu Val Asp Ala Lys Gly Cys Lys Lys
                20                  25                  30

Asn Cys Tyr Lys Leu Gly Lys Asn Asp Tyr Cys Asn Arg Glu Cys Arg
            35                  40                  45

Met Lys His Arg Gly Gly Ser Tyr Gly Tyr Cys Tyr Gly Phe Gly Cys
        50                  55                  60

Tyr Cys Glu Gly Leu Ser Asp Ser Thr Pro Thr Trp Pro Leu Pro Asn
65                  70                  75                  80

Lys Thr Cys Ser Gly Lys
                85
```

<210> SEQ ID NO 24
<211> LENGTH: 64
<212> TYPE: PRT
<213> ORGANISM: Centruroides sculpturatus

<400> SEQUENCE: 24

```
Lys Asp Gly Tyr Leu Val Glu Lys Thr Gly Cys Lys Lys Thr Cys Tyr
 1               5                  10                  15

Lys Leu Gly Glu Asn Asp Phe Cys Asn Arg Glu Cys Lys Trp Lys His
                20                  25                  30

Ile Gly Gly Ser Tyr Gly Tyr Cys Tyr Gly Phe Gly Cys Tyr Cys Glu
            35                  40                  45
```

```
Gly Leu Pro Asp Ser Thr Gln Thr Trp Pro Leu Pro Asn Lys Thr Cys
    50                  55                  60
```

<210> SEQ ID NO 25
<211> LENGTH: 70
<212> TYPE: PRT
<213> ORGANISM: Androctonus australis

<400> SEQUENCE: 25

```
Lys Lys Asn Gly Tyr Ala Val Asp Ser Ser Gly Lys Ala Pro Glu Cys
1               5                   10                  15

Leu Leu Ser Asn Tyr Cys Asn Asn Glu Cys Thr Lys Val His Tyr Ala
            20                  25                  30

Asp Lys Gly Tyr Cys Cys Leu Leu Ser Cys Tyr Cys Phe Gly Leu Asn
        35                  40                  45

Asp Asp Lys Lys Val Leu Glu Ile Ser Asp Thr Arg Lys Ser Tyr Cys
    50                  55                  60

Asp Thr Thr Ile Ile Asn
65                  70
```

<210> SEQ ID NO 26
<211> LENGTH: 70
<212> TYPE: PRT
<213> ORGANISM: Leiurus quinquestriatus quinquestriatus

<400> SEQUENCE: 26

```
Lys Lys Asn Gly Tyr Ala Val Asp Ser Ser Gly Lys Ala Pro Glu Cys
1               5                   10                  15

Leu Leu Ser Asn Tyr Cys Tyr Asn Glu Cys Thr Lys Val His Tyr Ala
            20                  25                  30

Asp Lys Gly Tyr Cys Cys Leu Leu Ser Cys Tyr Cys Val Gly Leu Ser
        35                  40                  45

Asp Asp Lys Lys Val Leu Glu Ile Ser Asp Ala Arg Lys Lys Tyr Cys
    50                  55                  60

Asp Phe Val Thr Ile Asn
65                  70
```

<210> SEQ ID NO 27
<211> LENGTH: 8
<212> TYPE: PRT
<213> ORGANISM: Parabuthus transvaalicus

<400> SEQUENCE: 27

```
Pro Phe Ile Val Pro Pro Phe Arg
1               5
```

<210> SEQ ID NO 28
<211> LENGTH: 8
<212> TYPE: PRT
<213> ORGANISM: Parabuthus transvaalicus
<220> FEATURE:
<221> NAME/KEY: METHYLATION
<222> LOCATION: (1)...(1)
<223> OTHER INFORMATION: N-terminal proline is modified.

<400> SEQUENCE: 28

```
Pro Phe Ile Val Pro Pro Phe Arg
1               5
```

<210> SEQ ID NO 29
<211> LENGTH: 8

```
<212> TYPE: PRT
<213> ORGANISM: Parabuthus transvaalicus

<400> SEQUENCE: 29

Pro Phe Val Val Pro Pro Phe Arg
 1               5

<210> SEQ ID NO 30
<211> LENGTH: 8
<212> TYPE: PRT
<213> ORGANISM: Parabuthus transvaalicus
<220> FEATURE:
<221> NAME/KEY: METHYLATION
<222> LOCATION: (1)...(1)
<223> OTHER INFORMATION: N-terminal Proline is modified.

<400> SEQUENCE: 30

Pro Phe Val Val Pro Pro Phe Arg
 1               5
```